US012735725B2

(12) United States Patent
Vandenberghe et al.

(10) Patent No.: US 12,735,725 B2

(45) **Date of Patent: *Sep. 15, 2026**

(54) ALTERING TISSUE TROPISM OF ADENO-ASSOCIATED VIRUSES

(71) Applicants: Massachusetts Eye and Ear Infirmary, Boston, MA (US); The Schepens Eye Research Institute, Inc., Boston, MA (US)

(72) Inventors: Luk H. Vandenberghe, Weston, MA (US); Pauline Schmit, Boston, MA (US); Christopher Tipper, Cambridge, MA (US); Carmen Unzu, Boston, MA (US); Eric Zinn, Lynn, MA (US)

(73) Assignees: Massachusetts Eye and Ear Infirmary, Boston, MA (US); The Schepens Eye Research Institute, Inc., Boston, MA (US)

( * ) Notice: Subject to any disclaimer, the term of this patent is extended or adjusted under 35 U.S.C. 154(b) by 320 days.

This patent is subject to a terminal disclaimer.

(21) Appl. No.: 18/633,726

(22) Filed: Apr. 12, 2024

(65) Prior Publication Data

US 2024/0344085 A1 Oct. 17, 2024

Related U.S. Application Data

(63) Continuation of application No. 17/053,412, filed as application No. PCT/US2019/031851 on May 10, 2019, now Pat. No. 11,987,801.

(60) Provisional application No. 62/841,179, filed on Apr. 30, 2019, provisional application No. 62/670,543, filed on May 11, 2018.

(51) Int. Cl.

| | |
|---|---|
| ***C12N 15/86*** | (2006.01) |
| ***C07K 14/005*** | (2006.01) |
| ***C12N 15/10*** | (2006.01) |

(52) U.S. Cl.

CPC ............ *C12N 15/86* (2013.01); *C07K 14/005* (2013.01); *C12N 15/102* (2013.01); *C12N 2750/14143* (2013.01)

(58) Field of Classification Search

None

See application file for complete search history.

(56) References Cited

U.S. PATENT DOCUMENTS

| | | | |
|---|---|---|---|
| 7,906,111 | B2 | 3/2011 | Wilson et al. |
| 9,695,220 | B2 | 7/2017 | Vandenberghe et al. |
| 9,719,070 | B2 | 8/2017 | Vandenberghe et al. |
| 10,077,291 | B2 | 9/2018 | Asokan et al. |
| 12,570,998 | B2 | 3/2026 | Zinn et al. |
| 2011/0104119 | A1 | 5/2011 | Bowles et al. |
| 2014/0060163 | A1 | 3/2014 | Watanabe et al. |
| 2015/0152142 | A1 | 6/2015 | Asokan et al. |
| 2016/0044819 | A1 | 2/2016 | Bailey et al. |
| 2017/0067908 | A1 | 3/2017 | Nakai et al. |
| 2017/0159026 | A1 | 6/2017 | Kay et al. |
| 2017/0348433 | A1 | 12/2017 | Kay et al. |
| 2018/0032166 | A1 | 2/2018 | Orihara |
| 2019/0031851 | A1 | 1/2019 | Uchida |
| 2019/0047546 | A1 | 2/2019 | Asai et al. |
| 2019/0367562 | A1 | 12/2019 | Asokan et al. |

FOREIGN PATENT DOCUMENTS

| | | | |
|---|---|---|---|
| CN | 103561774 | 2/2014 | |
| CN | 105247044 | 1/2016 | |
| CN | 106232618 | 12/2016 | |
| JP | 2016-533709 | 11/2016 | |
| WO | WO 2015/054653 | 4/2015 | |
| WO | WO-2015164757 A1 * | 10/2015 | ............ C12N 15/86 |
| WO | WO 2017/019994 | 2/2017 | |
| WO | WO 2017/100791 | 6/2017 | |
| WO | WO 2018/022608 | 2/2018 | |
| WO | WO 2018/071831 | 4/2018 | |
| WO | WO 2018/152333 | 8/2018 | |
| WO | WO 2018/209154 | 11/2018 | |
| WO | WO 2019/028306 A2 | 2/2019 | |
| WO | WO 2019/104279 | 5/2019 | |
| WO | WO 2019/217911 | 11/2019 | |
| WO | WO 2020/041498 | 2/2020 | |
| WO | WO 2021/050614 | 3/2021 | |
| WO | WO 2022/150634 | 7/2022 | |

OTHER PUBLICATIONS

Notice of Acceptance in Australian Appln. No. 2019264991, mailed on Nov. 19, 2025, 4 pages.
Office Action in Chinese Appln. No. 2020800779688, mailed on Sep. 20, 2025, 12 pages (with English translation).
Office Action in Australian Appln. No. 2019264991, mailed on Sep. 11, 2025, 4 pages.
Office Action in Japanese Appln. No. 2022-515606, mailed on Jun. 10, 2025, 19 pages (with English translation).
Office Action in Chinese Appln. No. 202080077968.8, mailed on Jan. 28, 2026, 15 pages (with English translation).
Office Action in Korean Appln. No. 10-2020-7035395, mailed on Dec. 11, 2025, 11 pages (with English translation).
Office Action in Korean Appln. No. 10-2020-7035395, mailed on Dec. 30, 2025, 6 pages (with English Translation).
Office Action in Brazillian Appln. No. BR112020022858-3, mailed on Mar. 3, 2026, 10 pages (with English translation).
Office Action in Indian Patent Appln. 202047050454, mailed on Mar. 27, 2026, 6 pages (with English translation).
Office Action in Australian Appln. No. 2019264991, mailed on Feb. 6, 2025, 4 pages.
Office Action in Korean Appln. No. 10-2020-7035395, mailed on Jan. 21, 2025, 10 pages (with English translation).
Office Action in Japanese Appln. No. 2024-020029, mailed on Feb. 25, 2025, 9 pages (with English translation).

(Continued)

*Primary Examiner* — Manjunath N Rao

*Assistant Examiner* — Jae W Lee

(74) *Attorney, Agent, or Firm* — Fish & Richardson P.C.

(57) ABSTRACT

This disclosure provides compositions and methods for altering or changing the tissue tropism, e.g., liver tropism, of adeno-associated viruses (AAV).

6 Claims, 28 Drawing Sheets

Specification includes a Sequence Listing.

(56) References Cited

OTHER PUBLICATIONS

Advances in Molecular Biophotonics, Shanghai Jio Tong University Press, Luo Qingming (ed)., Oct. 31, 2014, p. 191, 5 pages (with English translation).
Office Action in Chinese Appln. No. 201980042499.3, dated Jun. 28, 2024, 30 pages (with English translation).
Office Action in Israeli Appln. No. 278598, dated Jul. 9, 2024, 4 pages.
Office Action in Chinese Appln. No. 201980042499.3, mailed on Nov. 14, 2024, 24 pages (with English translation).
Office Action in European Appln. No. 20789739.8, mailed on Nov. 19, 2024, 4 pages.
Office Action in Japanese Appln. No. 2022-515606, mailed on Sep. 10, 2024, 25 pages (with English translation).
Genbank Accession No. QDH44216.1, "major coat protein VP1 [Adeno-associated virus]," Jul. 7, 2019, 2 pages.
Office Action in Canadian Appln. No. 3,153,972, mailed on Jan. 7, 2025, 7 pages.
Office Action in Chinese Appln. No. 2020800779688, mailed on Dec. 31, 2024, 21 pages (with English translation).
Zincarelli et al., "Analysis of AAV serotypes 1-9 mediated gene expression and tropism in mice after systemic injection," Mol. Ther., Jun. 2008, 16(6):1073-1080.
Albright et al., "Mapping the Structural Determinants Required for AAVrh.10 Transport across the Blood-Brain Barrier," Molecular Therapy, 2018, 26(2), 21 pages.
Altschul et al., "Gapped BLAST and PSI-BLAST: A new generation of protein database search programs," Nucleic Acids Res., 1997, 25(17):3389-3402.
Bowles et al., "Marker Rescue of Adeno-Associated Virus (AAV) Capsid Mutants: a Novel Approach for Chimeric AAV Production," J. Virol., 2003, 77:423-432.
Bowles et al., "Phase 1 Gene Therapy for Duchenne Muscular Dystrophy Using a Translational Optimized AAV Vector," Molecular Therapy, Feb. 2012, 20(2):443-455.
Dayhoff et al., "22: A model of evolutionary change in proteins," Atlas of protein sequence and structure, vol. 5, National Biomedical Research Foundation Silver Spring, 1978, pp. 345-352.
Drouin et al., "Adeno-associated virus structural biology as a tool in vector development," Future Virology, Dec. 2013, 8(12):1183-1199.
Dudek et al., "An Alternate Route for Adeno-associated Virus (AAV) Entry Independent of AAV Receptor," J. Virol., Mar. 2018, 92(7):e02213-17, 15 pages.
Edgar, "Muscle: multiple sequence alignment with high accuracy and high throughput," Nucleic Acids Res., Mar. 2004, 32(5):1792-1797.
Extended European Search Report in European Appln. No. 19799988.1, dated Oct. 28, 2021, 7 pages.
Flytzanis et al., "Abstract 102: Engineered AAVS for CNS Transduction and Peripheral Organ De-Targeting across Species after Systemic Delivery," Molecular Therapy, Apr. 2019, 27(4S1):54.
Grimm et al., "In vitro and in vivo gene therapy vector evolution via multispecies interbreeding and retargeting of adeno-associated viruses," J. Virol., 2008, 82(12):5887-911.
International Preliminary Report on Patentability in International Application No. PCT/US2019/031851, mailed Nov. 26, 2020, 6 pages.
International Preliminary Report on Patentability in International Application No. PCT/US2020/050027, mailed Mar. 9, 2022, 10 pages.
International Preliminary Report on Patentability in International Appln. No. PCT/US2022/011682, mailed Jul. 20, 2023, 14 pages.
International Search Report and Written Opinion in International Appln. No. PCT/US2019/031851, mailed Aug. 29, 2019, 8 pages.
International Search Report and Written Opinion in International Appln. No. PCT/US2020/050027, mailed Apr. 13, 2021, 18 pages.
International Search Report and Written Opinion in International Appln. No. PCT/US2022/011682, mailed Jul. 4, 2022, 24 pages.
Invitation to Pay Additional Fees and, Where Applicable, Protest Fee in International Appln. No. PCT/US2020/050027, mailed Feb. 22, 2021, 11 pages.
Invitation to Pay Additional Fees and, Where Applicable, Protest Fee in International Appln. No. PCT/US2022/011682, mailed May 13, 2022, 19 pages.
Kumar et al., "Abstract 99: Multiplexed-Create Selection Yields AAV Vectors Targeting Different Cell Types of the Central Nervous System Following Systemic Delivery," Molecular Therapy, Apr. 2019, 27(4S1):53.
Ling et al., "Human Hepatocyte Growth Factor Receptor Is a Cellular Coreceptor for Adeno-Associated Virus Serotype 3," Hum. Gene. Ther., 2010, 21(12)1741-1747.
Lisowski et al., "Selection and evaluation of clinically relevant AAV variants in a xenograft liver model," Nature, 2014, 506:382-386.
Lochrie et al., "Mutations on the external surfaces of adeno-associated virus type 2 capsids that affect transduction and neutralization," Journal of Virology, Jan. 2006, 80(2):821-834.
Meyer et al., "Structure of the gene therapy vector, adeno-associated virus with its cell receptor, AAVR," ELife, May 2019, 8:e44707, 24 pages.
Nam et al., "Structure of adeno-associated virus serotype 8, a gene therapy vector," J. Virol., 2007, 81(22):12260-71.
Notice of Allowance in Japanese Appln. No. 2020-563602, dated Jan. 16, 2024, 5 pages (with English translation).
Office Action in Canadian Appln. No. 3,100,006, dated Oct. 11, 2023, 3 pages.
Office Action in Canadian Appln. No. 3153972, dated Oct. 26, 2023, 5 pages.
Office Action in Chinese Appln. No. 201980042499.3, dated Oct. 19, 2023, 34 pages (with English translation).
Office Action in Japanese Appln. No. 2020-563602, dated Aug. 29, 2023, 8 pages (with English translation).
Office Action in Japanese Appln. No. 2020-563602, dated Feb. 14, 2023, 11 pages (with English translation).
Office Action in Saudi Arabian Appln. No. 520420518, dated Dec. 13, 2022, 13 pages (with English machine translation).
Office Action in Saudi Arabian Appln. No. 520420518, dated Mar. 15, 2022, 14 pages (with English machine translation).
Pillay et al., "An essential receptor for adeno-associated virus infection," Nature, Feb. 2016, 530(7588):108-12, 16 pages.
Raupp et al., "The Threefold Protrusions of Adeno-Associated Virus Type 8 Are Involved in Cell Surface Targeting as Well as Postattachment Processing," J. Virol., 2012, 86(17):9396-408.
Wu et al., "Single amino acid changes can influence titer, heparin binding, and tissue tropism in different adeno-associated virus serotypes," J. Virol., 2006, 80(22):11393-7.
Zhang et al., "Adeno-associated virus 2 bound to its cellular receptor AAVR," Nat. Microbiol., Apr. 2019, 4(4):675-682, 10 pages.
Zinn et al., "In Silico Reconstruction of the Viral Evolutionary Lineage Yields a Potent Gene Therapy Vector," Cell Rep., Aug. 2015, 12(6):1056-1068.

* cited by examiner

SEQ ID NO:1 Anc80

MAADGYLPDWLEDNLSEGIREWWDLKPGAPKPKANQQKQDDGRGLVLPGYKYLGPFNGLDKGEPVNAADAAALE
HDKAYDQQLKAGDNPYLRYNHADAEFQERLQEDTSFGGNLGRAVFQAKKRVLEPLGLVEEGAKTAPGKKRPVEQSP
QEPDSSSGIGKKGQQPA$X_1$KRLNFGQTGDSESVPDPQPLGEPPAAPSGVGSNTM$X_2$AGGGAPMADNNEGADGVG
NASGNWHCDSTWLGDRVITTSTRTWALPTYNNHLYKQISSQSG$X_3$STNDNTYFGYSTPWGYFDFNRFHCHFSPRD
WQRLINNNWGFRPK$X_4$LNFKLFNIQVKEVTTNDGTTTIANNLTSTVQVFTDSEYQLPYVLGSAHQGCLPPFPADVFM
IPQYGYLTLNNGSQAVGRSSFYCLEYFPSQMLRTGNNF$X_5$FSYTFEDVPFHSSYAHSQSLDRLMNPLIDQYLYYLSRTQ
TTSGTAGNR$X_6$LQFSQAGPSSMANQAKNWLPGPCYRQQRVSKT$X_7$NQNNNSNFAWTGATKYHLNGRDSLVNPGP
AMATHKDDEDKFFPMSGVLIFGKQGAGNSNVDLDNVMIT$X_8$EEEIKTTNPVATE$X_9$YGTVATNLQS$X_{10}$NTAPATGT
VNSQGALPGMVWQ$X_{11}$RDVYLQGPIWAKIPHTDGHFHPSPLMGGFGLKHPPPQILIKNTPVPANPPTTFSPAKFASF
ITQYSTGQVSVEIEWELQKENSKRWNPEIQYTSNYNKSTNVDFAVDTNGVYSEPRPIGTRYLTRNL

| | | |
|---|---|---|
| **$X_1$ = K/R** | $X_5$ = E/Q | $X_9$ = Q/E |
| $X_2$ = A/S | $X_6$ = T/E | $X_{10}$ = S/A |
| **$X_3$ = A/G** | $X_7$ = A/T | $X_{11}$ = N/D |
| $X_4$ = R/K | $X_8$ = S/N | |

FIG. 1

SEQ ID NO:2 Anc80L65_VP1

MAADGYLPDWLEDNLSEGIREWWDLKPGAPKPKANQQKQDDGRGLVLPGYKYLGPFNGLDKGEPVNAADAAALE
HDKAYDQQLKAGDNPYLRYNHADAEFQERLQEDTSFGGNLGRAVFQAKKRVLEPLGLVEEGAKTAPGKKRPVEQSP
QEPDSSSGIGKKGQQPARKRLNFGQTGDSESVPDPQPLGEPPAAPSGVGSNTMAAGGGAPMADNNEGADGVGN
ASGNWHCDSTWLGDRVITTSTRTWALPTYNNHLYKQISSQSGGSTNDNTYFGYSTPWGYFDFNRFHCHFSPRDW
QRLINNNWGFRPKKLNFKLFNIQVKEVTTNDGTTTIANNLTSTVQVFTDSEYQLPYVLGSAHQGCLPPFPADVFMIP
QYGYLTLNNGSQAVGRSSFYCLEYFPSQMLRTGNNFQFSYTFEDVPFHSSYAHSQSLDRLMNPLIDQYLYYLSRTQTT
SGTAGNRTLQFSQAGPSSMANQAKNWLPGPCYRQQRVSKTTNQNNNSNFAWTGATKYHLNGRDSLVNPGPAM
ATHKDDEDKFFPMSGVLIFGKQGAGNSNVDLDNVMITNEEEIKTTNPVATEEYGTVATNLQSANTAPATGTVNSQG
ALPGMVWQDRDVYLQGPIWAKIPHTDGHFHPSPLMGGFGLKHPPPQILIKNTPVPANPPTTFSPAKFASFITQYSTG
QVSVEIEWELQKENSKRWNPEIQYTSNYNKSTNVDFAVDTNGVYSEPRPIGTRYLTRNL

FIG. 2A

SEQ ID NO:3 Anc80L65_G266A_VP1

MAADGYLPDWLEDNLSEGIREWWDLKPGAPKPKANQQKQDDGRGLVLPGYKYLGPFNGLDKGEPVNAADAAALE
HDKAYDQQLKAGDNPYLRYNHADAEFQERLQEDTSFGGNLGRAVFQAKKRVLEPLGLVEEGAKTAPGKKRPVEQSP
QEPDSSSGIGKKGQQPARKRLNFGQTGDSESVPDPQPLGEPPAAPSGVGSNTMAAGGGAPMADNNEGADGVGN
ASGNWHCDSTWLGDRVITTSTRTWALPTYNNHLYKQISSQSGASTNDNTYFGYSTPWGYFDFNRFHCHFSPRDWQ
RLINNNWGFRPKKLNFKLFNIQVKEVTTNDGTTTIANNLTSTVQVFTDSEYQLPYVLGSAHQGCLPPFPADVFMIPQY
GYLTLNNGSQAVGRSSFYCLEYFPSQMLRTGNNFQFSYTFEDVPFHSSYAHSQSLDRLMNPLIDQYLYYLSRTQTTSG
TAGNRTLQFSQAGPSSMANQAKNWLPGPCYRQQRVSKTTNQNNNSNFAWTGATKYHLNGRDSLVNPGPAMAT
HKDDEDKFFPMSGVLIFGKQGAGNSNVDLDNVMITNEEEIKTTNPVATEEYGTVATNLQSANTAPATGTVNSQGAL
PGMVWQDRDVYLQGPIWAKIPHTDGHFHPSPLMGGFGLKHPPPQILIKNTPVPANPPTTFSPAKFASFITQYSTGQV
SVEIEWELQKENSKRWNPEIQYTSNYNKSTNVDFAVDTNGVYSEPRPIGTRYLTRNL

FIG. 2B

SEQ ID NO:4 AAV9_G267A

MAADGYLPDWLEDNLSEGIREWWALKPGAPQPKANQQHQDNARGLVLPGYKYLGPGNGLDKGEPVNAADAAAL
EHDKAYDQQLKAGDNPYLKYNHADAEFQERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGSLTMASGGGAPVADNNEGADGVGSSS
GNWHCDSQWLGDRVITTSTRTWALPTYNNHLYKQISNSTSGASSNDNAYFGYSTPWGYFDFNRFHCHFSPRDWQ
RLINNNWGFRPKRLNFKLFNIQVKEVTDNNGVKTIANNLTSTVQVFTDSDYQLPYVLGSAHEGCLPPFPADVFMIPQ
YGYLTLNDGSQAVGRSSFYCLEYFPSQMLRTGNNFQFSYEFENVPFHSSYAHSQSLDRLMNPLIDQYLYYLSKTINGS
GQNQQTLKFSVAGPSNMAVQGRNYIPGPSYRQQRVSTTVTQNNNSEFAWPGASSWALNGRNSLMNPGPAMAS
HKEGEDRFFPLSGSLIFGKQGTGRDNVDADKVMITNEEEIKTTNPVATESYGQVATNHQSAQAQAQTGWVQNQGI
LPGMVWQDRDVYLQGPIWAKIPHTDGNFHPSPLMGGFGMKHPPPQILIKNTPVPADPPTAFNKDKLNSFITQYSTG
QVSVEIEWELQKENSKRWNPEIQYTSNYYKSNNVEFAVNTEGVYSEPRPIGTRYLTRNL

FIG. 3A

SEQ ID NO:5 AAV9_G267A, S269T

MAADGYLPDWLEDNLSEGIREWWALKPGAPQPKANQQHQDNARGLVLPGYKYLGPGNGLDKGEPVNAADAAAL
EHDKAYDQQLKAGDNPYLKYNHADAEFQERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGSLTMASGGGAPVADNNEGADGVGSSS
GNWHCDSQWLGDRVITTSTRTWALPTYNNHLYKQISNSTSGASTNDNAYFGYSTPWGYFDFNRFHCHFSPRDWQ
RLINNNWGFRPKRLNFKLFNIQVKEVTDNNGVKTIANNLTSTVQVFTDSDYQLPYVLGSAHEGCLPPFPADVFMIPQ
YGYLTLNDGSQAVGRSSFYCLEYFPSQMLRTGNNFQFSYEFENVPFHSSYAHSQSLDRLMNPLIDQYLYYLSKTINGS
GQNQQTLKFSVAGPSNMAVQGRNYIPGPSYRQQRVSTTVTQNNNSEFAWPGASSWALNGRNSLMNPGPAMAS
HKEGEDRFFPLSGSLIFGKQGTGRDNVDADKVMITNEEEIKTTNPVATESYGQVATNHQSAQAQAQTGWVQNQGI
LPGMVWQDRDVYLQGPIWAKIPHTDGNFHPSPLMGGFGMKHPPPQILIKNTPVPADPPTAFNKDKLNSFITQYSTG
QVSVEIEWELQKENSKRWNPEIQYTSNYYKSNNVEFAVNTEGVYSEPRPIGTRYLTRNL

FIG. 3B

SEQ ID NO:6 AAV9 Anc80L65-VRI

MAADGYLPDWLEDNLSEGIREWWALKPGAPQPKANQQHQDNARGLVLPGYKYLGPGNGLDKGEPVNAADAAAL
EHDKAYDQQLKAGDNPYLKYNHADAEFQERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGSLTMASGGGAPVADNNEGADGVGSSS
GNWHCDSQWLGDRVITTSTRTWALPTYNNHLYKQISSQSGGSTNDNTYFGYSTPWGYFDFNRFHCHFSPRDWQR
LINNNWGFRPKRLNFKLFNIQVKEVTDNNGVKTIANNLTSTVQVFTDSDYQLPYVLGSAHEGCLPPFPADVFMIPQY
GYLTLNDGSQAVGRSSFYCLEYFPSQMLRTGNNFQFSYEFENVPFHSSYAHSQSLDRLMNPLIDQYLYYLSKTINGSG
QNQQTLKFSVAGPSNMAVQGRNYIPGPSYRQQRVSTTVTQNNNSEFAWPGASSWALNGRNSLMNPGPAMASH
KEGEDRFFPLSGSLIFGKQGTGRDNVDADKVMITNEEEIKTTNPVATESYGQVATNHQSAQAQAQTGWVQNQGIL
PGMVWQDRDVYLQGPIWAKIPHTDGNFHPSPLMGGFGMKHPPPQILIKNTPVPADPPTAFNKDKLNSFITQYSTG
QVSVEIEWELQKENSKRWNPEIQYTSNYYKSNNVEFAVNTEGVYSEPRPIGTRYLTRNL

FIG. 4A

SEQ ID NO:7 AAV9 Anc80L65 G266A-VRI

MAADGYLPDWLEDNLSEGIREWWALKPGAPQPKANQQHQDNARGLVLPGYKYLGPGNGLDKGEPVNAADAAAL
EHDKAYDQQLKAGDNPYLKYNHADAEFQERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGSLTMASGGGAPVADNNEGADGVGSSS
GNWHCDSQWLGDRVITTSTRTWALPTYNNHLYKQISSQSGASTNDNTYFGYSTPWGYFDFNRFHCHFSPRDWQR
LINNNWGFRPKRLNFKLFNIQVKEVTDNNGVKTIANNLTSTVQVFTDSDYQLPYVLGSAHEGCLPPFPADVFMIPQY
GYLTLNDGSQAVGRSSFYCLEYFPSQMLRTGNNFQFSYEFENVPFHSSYAHSQSLDRLMNPLIDQYLYYLSKTINGSG
QNQQTLKFSVAGPSNMAVQGRNYIPGPSYRQQRVSTTVTQNNNSEFAWPGASSWALNGRNSLMNPGPAMASH
KEGEDRFFPLSGSLIFGKQGTGRDNVDADKVMITNEEEIKTTNPVATESYGQVATNHQSAQAQAQTGWVQNQGIL
PGMVWQDRDVYLQGPIWAKIPHTDGNFHPSPLMGGFGMKHPPPQILIKNTPVPADPPTAFNKDKLNSFITQYSTG
QVSVEIEWELQKENSKRWNPEIQYTSNYYKSNNVEFAVNTEGVYSEPRPIGTRYLTRNL

FIG. 4B

SEQ ID NO:8 AAV3B_A266G

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISSQSGGSNDNHYFGYSTPWGYFDFNRFHCHFSPRDWQ
RLINNNWGFRPKKLSFKLFNIQVKEVTQNDGTTTIANNLTSTVQVFTDSEYQLPYVLGSAHQGCLPPFPADVFMVPQ
YGYLTLNNGSQAVGRSSFYCLEYFPSQMLRTGNNFQFSYTFEDVPFHSSYAHSQSLDRLMNPLIDQYLYYLNRTQGTT
SGTTNQSRLLFSQAGPQSMSLQARNWLPGPCYRQQRLSKTANDNNNSNFPWTAASKYHLNGRDSLVNPGPAMAS
HKDDEEKFFPMHGNLIFGKEGTTASNAELDNVMITDEEEIRTTNPVATEQYGTVANNLQSSNTAPTTRTVNDQGALP
GMVWQDRDVYLQGPIWAKIPHTDGHFHPSPLMGGFGLKHPPPQIMIKNTPVPANPPTTFSPAKFASFITQYSTGQV
SVEIEWELQKENSKRWNPEIQYTSNYNKSVNVDFTVDTNGVYSEPRPIGTRYLTRNL

FIG. 5A

SEQ ID NO:9 AAV3B_A266G, S267_N268T

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISSQSGGSTNDNHYFGYSTPWGYFDFNRFHCHFSPRDW
QRLINNNWGFRPKKLSFKLFNIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFQFSYTFEDVPFHSSYAHSQSLDRLMNPLIDQYLYYLNRTQG
TTSGTTNQSRLLFSQAGPQSMSLQARNWLPGPCYRQQRLSKTANDNNNSNFPWTAASKYHLNGRDSLVNPGPAM
ASHKDDEEKFFPMHGNLIFGKEGTTASNAELDNVMITDEEEIRTTNPVATEQYGTVANNLQSSNTAPTTRTVNDQG
ALPGMVWQDRDVYLQGPIWAKIPHTDGHFHPSPLMGGFGLKHPPPQIMIKNTPVPANPPTTFSPAKFASFITQYST
GQVSVEIEWELQKENSKRWNPEIQYTSNYNKSVNVDFTVDTNGVYSEPRPIGTRYLTRNL

FIG. 5B

SEQ ID NO:10 AAV3B G265_A266A

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISSQSGAASNDNHYFGYSTPWGYFDFNRFHCHFSPRDW
QRLINNNWGFRPKKLSFKLFNIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFQFSYTFEDVPFHSSYAHSQSLDRLMNPLIDQYLYYLNRTQG
TTSGTTNQSRLLFSQAGPQSMSLQARNWLPGPCYRQQRLSKTANDNNNSNFPWTAASKYHLNGRDSLVNPGPAM
ASHKDDEEKFFPMHGNLIFGKEGTTASNAELDNVMITDEEEIRTTNPVATEQYGTVANNLQSSNTAPTTRTVNDQG
ALPGMVWQDRDVYLQGPIWAKIPHTDGHFHPSPLMGGFGLKHPPPQIMIKNTPVPANPPTTFSPAKFASFITQYST
GQVSVEIEWELQKENSKRWNPEIQYTSNYNKSVNVDFTVDTNGVYSEPRPIGTRYLTRNL

FIG. 6A

SEQ ID NO:11 AAV3B G265_A266G

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISSQSGGASNDNHYFGYSTPWGYFDFNRFHCHFSPRDW
QRLINNNWGFRPKKLSFKLFNIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFQFSYTFEDVPFHSSYAHSQSLDRLMNPLIDQYLYYLNRTQG
TTSGTTNQSRLLFSQAGPQSMSLQARNWLPGPCYRQQRLSKTANDNNNSNFPWTAASKYHLNGRDSLVNPGPAM
ASHKDDEEKFFPMHGNLIFGKEGTTASNAELDNVMITDEEEIRTTNPVATEQYGTVANNLQSSNTAPTTRTVNDQG
ALPGMVWQDRDVYLQGPIWAKIPHTDGHFHPSPLMGGFGLKHPPPQIMIKNTPVPANPPTTFSPAKFASFITQYST
GQVSVEIEWELQKENSKRWNPEIQYTSNYNKSVNVDFTVDTNGVYSEPRPIGTRYLTRNL

FIG. 6B

SEQ ID NO:12 AAV3B G265_A266A S268T

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISSQSGAATNDNHYFGYSTPWGYFDFNRFHCHFSPRDW
QRLINNNWGFRPKKLSFKLFNIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFQFSYTFEDVPFHSSYAHSQSLDRLMNPLIDQYLYYLNRTQG
TTSGTTNQSRLLFSQAGPQSMSLQARNWLPGPCYRQQRLSKTANDNNNSNFPWTAASKYHLNGRDSLVNPGPAM
ASHKDDEEKFFPMHGNLIFGKEGTTASNAELDNVMITDEEEIRTTNPVATEQYGTVANNLQSSNTAPTTRTVNDQG
ALPGMVWQDRDVYLQGPIWAKIPHTDGHFHPSPLMGGFGLKHPPPQIMIKNTPVPANPPTTFSPAKFASFITQYST
GQVSVEIEWELQKENSKRWNPEIQYTSNYNKSVNVDFTVDTNGVYSEPRPIGTRYLTRNL

FIG. 7A

SEQ ID NO:13 AAV3B G265_A266G S268T

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISSQSGGATNDNHYFGYSTPWGYFDFNRFHCHFSPRDW
QRLINNNWGFRPKKLSFKLFNIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFQFSYTFEDVPFHSSYAHSQSLDRLMNPLIDQYLYYLNRTQG
TTSGTTNQSRLLFSQAGPQSMSLQARNWLPGPCYRQQRLSKTANDNNNSNFPWTAASKYHLNGRDSLVNPGPAM
ASHKDDEEKFFPMHGNLIFGKEGTTASNAELDNVMITDEEEIRTTNPVATEQYGTVANNLQSSNTAPTTRTVNDQG
ALPGMVWQDRDVYLQGPIWAKIPHTDGHFHPSPLMGGFGLKHPPPQIMIKNTPVPANPPTTFSPAKFASFITQYST
GQVSVEIEWELQKENSKRWNPEIQYTSNYNKSVNVDFTVDTNGVYSEPRPIGTRYLTRNL

FIG. 7B

SEQ ID NO:14 AAV3B AAV9-VRI

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISNSTSGGSSNDNAYFGYSTPWGYFDFNRFHCHFSPRD
WQRLINNNWGFRPKKLSFKLFNIQVKEVTQNDGTTTIANNLTSTVQVFTDSEYQLPYVLGSAHQGCLPPFPADVFM
VPQYGYLTLNNGSQAVGRSSFYCLEYFPSQMLRTGNNFQFSYTFEDVPFHSSYAHSQSLDRLMNPLIDQYLYYLNRT
QGTTSGTTNQSRLLFSQAGPQSMSLQARNWLPGPCYRQQRLSKTANDNNNSNFPWTAASKYHLNGRDSLVNPGP
AMASHKDDEEKFFPMHGNLIFGKEGTTASNAELDNVMITDEEEIRTTNPVATEQYGTVANNLQSSNTAPTTRTVND
QGALPGMVWQDRDVYLQGPIWAKIPHTDGHFHPSPLMGGFGLKHPPPQIMIKNTPVPANPPTTFSPAKFASFITQY
STGQVSVEIEWELQKENSKRWNPEIQYTSNYNKSVNVDFTVDTNGVYSEPRPIGTRYLTRNL

FIG. 8A

SEQ ID NO:15 AAV3B Anc80L65-VRI

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISSQSGGSTNDNTYFGYSTPWGYFDFNRFHCHFSPRDW
QRLINNNWGFRPKKLSFKLFNIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFQFSYTFEDVPFHSSYAHSQSLDRLMNPLIDQYLYYLNRTQG
TTSGTTNQSRLLFSQAGPQSMSLQARNWLPGPCYRQQRLSKTANDNNNSNFPWTAASKYHLNGRDSLVNPGPAM
ASHKDDEEKFFPMHGNLIFGKEGTTASNAELDNVMITDEEEIRTTNPVATEQYGTVANNLQSSNTAPTTRTVNDQG
ALPGMVWQDRDVYLQGPIWAKIPHTDGHFHPSPLMGGFGLKHPPPQIMIKNTPVPANPPTTFSPAKFASFITQYST
GQVSVEIEWELQKENSKRWNPEIQYTSNYNKSVNVDFTVDTNGVYSEPRPIGTRYLTRNL

FIG. 8B

SEQ ID NO:16 AAV3B Anc80L65 G266A-VRI

MAADGYLPDWLEDNLSEGIREWWALKPGVPQPKANQQHQDNRRGLVLPGYKYLGPGNGLDKGEPVNEADAAAL
EHDKAYDQQLKAGDNPYLKYNHADAEFQERLQEDTSFGGNLGRAVFQAKKRILEPLGLVEEAAKTAPGKKRPVDQS
PQEPDSSSGVGKSGKQPARKRLNFGQTGDSESVPDPQPLGEPPAAPTSLGSNTMASGGGAPMADNNEGADGVGN
SSGNWHCDSQWLGDRVITTSTRTWALPTYNNHLYKQISSQSGASTNDNTYFGYSTPWGYFDFNRFHCHFSPRDW
QRLINNNWGFRPKKLSFKLFNIQVKEVTQNDGTTTIANNLTSTVQVFTDSEYQLPYVLGSAHQGCLPPFPADVFMVP
QYGYLTLNNGSQAVGRSSFYCLEYFPSQMLRTGNNFQFSYTFEDVPFHSSYAHSQSLDRLMNPLIDQYLYYLNRTQG
TTSGTTNQSRLLFSQAGPQSMSLQARNWLPGPCYRQQRLSKTANDNNNSNFPWTAASKYHLNGRDSLVNPGPAM
ASHKDDEEKFFPMHGNLIFGKEGTTASNAELDNVMITDEEEIRTTNPVATEQYGTVANNLQSSNTAPTTRTVNDQGS
LPGMVWQDRDVYLQGPIWAKIPHTDGHFHPSPLMGGFGLKHPPPQIMIKNTPVPANPPTTFSPAKFASFITQYSTG
QVSVEIEWELQKENSKRWNPEIQYTSNYNKSVNVDFTVDTNGVYSEPRPIGTRYLTRNL

FIG. 8C

| Code | X1 | X2 | X3 | X4 | X5 | X6 | X7 | X8 | X9 | X10 | X11 |
|---|---|---|---|---|---|---|---|---|---|---|---|
| 0 | K | A | A | K | Q | T | T | N | Q | A | N |
| 1 | R | S | G | R | E | E | A | S | E | S | D |

| Code | X1 | X2 | X3 | X4 | X5 | X6 | X7 | X8 | X9 | X10 | X11 |
|---|---|---|---|---|---|---|---|---|---|---|---|
| 0 | K | A | A | K | Q | T | T | N | Q | A | N |
| 1 | R | S | G | R | E | E | A | S | E | S | D |

| Code | X1 | X2 | X3 | X4 | X5 | X6 | X7 | X8 | X9 | X10 | X11 |
|---|---|---|---|---|---|---|---|---|---|---|---|
| 0 | K | A | A | K | Q | T | T | N | Q | A | N |
| 1 | R | S | G | R | E | E | A | S | E | S | D |
| Anc80L65 | R | A | **G** | K | Q | T | T | N | E | A | D |
| Anc80L65 G266A | R | A | **A** | K | Q | T | T | N | E | A | D |

| Serotype | Toggle Region | Altera ons | M | P |
|---|---|---|---|---|
| Anc80L65 | -SQSGGST NDN | | **on** | **on** |
| | -SQSG**A**ST NDN | G266A | **off** | **off** |
| AAV3B | -SQS-GAS- NDN<br>-SQSG-AS NDN | <br>Alt. indel alignment | **off** | **on** |
| | -SQS-G**G**S- NDN | A266G | *on* | *on* |
| | -SQSGAS**T** NDN | S267_N268T | | |
| | -SQSG**G**S**T** NDN | A266G, S267_N268T | *on* | *on* |
| | -S-QS-GA**T** NDN | S268T | | |
| | -SQSG**A**AS NDN | G265_A266A | **off** | *off* |
| | -SQSG**G**AS NDN | G265_A266G | **on** | *on* |
| | -SQSG**A**A**T** NDN | G265_A266A, S268T | *off* | *off* |
| | -SQSG**G**A**T** NDN | G265_A266G, S268T | *on* | *on* |
| AAV9 | NSTSGGSS NDN | | **on** | **on** |
| | NSTSG**A**SS NDN | G267A | **off** | *off* |
| | NSTSGGS**T** NDN | S269T | | |
| | NSTSG**A**S**T** NDN | G267A, S269T | **off** | *off* |

FIG. 15

| Serotype | Toggle Region Source | Toggle Region Sequence | M | P |
|---|---|---|---|---|
| AAV9 | Anc80L65 | -SQSGGST NDN | **on** | *on* |
| | Anc80 L65 G266A | -SQSG<u>**A**</u>ST NDN | **off** | *off* |
| | AAV3B | -SQS-GAS- NDN | **off** | *on* |
| AAV3B | Anc80L65 | -SQSGGST NDN | **on** | *on* |
| | Anc80 L65 G266A | -SQSG<u>**A**</u>ST NDN | **off** | *off* |
| | AAV9 | NSTSGGSS NDN | **on** | *on* |
| Anc80L65 | AAV9 | NSTSGGSS NDN | *on* | *on* |
| | AAV3B | -SQS-GAS- NDN | *off* | *off* |

FIG. 17

SEQ ID NO:17 Anc80L65_R168K_VP1

MAADGYLPDWLEDNLSEGIREWWDLKPGAPKPKANQQKQDDGRGLVLPGYKYLGPFNGLDKGEPVNAADAAALE
HDKAYDQQLKAGDNPYLRYNHADAEFQERLQEDTSFGGNLGRAVFQAKKRVLEPLGLVEEGAKTAPGKKRPVEQSP
QEPDSSSGIGKKGQQPAKKRLNFGQTGDSESVPDPQPLGEPPAAPSGVGSNTMAAGGGAPMADNNEGADGVGN
ASGNWHCDSTWLGDRVITTSTRTWALPTYNNHLYKQISSQSGGSTNDNTYFGYSTPWGYFDFNRFHCHFSPRDWQ
RLINNNWGFRPKKLNFKLFNIQVKEVTTNDGTTTIANNLTSTVQVFTDSEYQLPYVLGSAHQGCLPPFPADVFMIPQY
GYLTLNNGSQAVGRSSFYCLEYFPSQMLRTGNNFQFSYTFEDVPFHSSYAHSQSLDRLMNPLIDQYLYYLSRTQTTSG
TAGNRTLQFSQAGPSSMANQAKNWLPGPCYRQQRVSKTTNQNNNSNFAWTGATKYHLNGRDSLVNPGPAMAT
HKDDEDKFFPMSGVLIFGKQGAGNSNVDLDNVMITNEEEIKTTNPVATEEYGTVATNLQSANTAPATGTVNSQGAL
PGMVWQDRDVYLQGPIWAKIPHTDGHFHPSPLMGGFGLKHPPPQILIKNTPVPANPPTTFSPAKFASFITQYSTGQV
SVEIEWELQKENSKRWNPEIQYTSNYNKSTNVDFAVDTNGVYSEPRPIGTRYLTRNL

FIG. 23

| Code | X1 | X2 | X3 | X4 | X5 | X6 | X7 | X8 | X9 | X10 | X11 |
|---|---|---|---|---|---|---|---|---|---|---|---|
| 0 | K | A | A | K | Q | T | T | N | Q | A | N |
| 1 | R | S | G | R | E | E | A | S | E | S | D |

ALTERING TISSUE TROPISM OF ADENO-ASSOCIATED VIRUSES

CROSS-REFERENCE TO RELATED APPLICATIONS

This application is a Continuation of U.S. application Ser. No. 17/053,412, filed Nov. 6, 2020, which is a 371 U.S. National Stage entry of International Application No. PCT/US2019/031851, filed on May 10, 2019, which claims priority to U.S. Application No. 62/841,179, filed on Apr. 30, 2019, and to U.S. Application No. 62/670,543, filed on May 11, 2018.

SEQUENCE LISTING

This application contains a Sequence Listing that has been submitted electronically as an XML file named "49998-0255002_SL_ST26.XML." The XML file, created on Apr. 10, 2026, is 100,321 bytes in size. The material in the XML file is hereby incorporated by reference in its entirety.

TECHNICAL FIELD

This disclosure generally relates to altering tissue tropism of adeno-associated virus (AAV) and specifically to controlling liver tropism of AAV.

BACKGROUND

Adeno-associated virus (AAV) is a small virus that belongs to the genus Dependoparvovirus, which in turn belongs to the family Parvoviridae. The virus is a replication-defective, non-enveloped virus that infects, but is not known to cause disease in, humans and certain primate species. AAV can infect both dividing and quiescent cells and persist in an extrachromosomal state without integrating into the genome of the host cell, although in the native virus, some integration of virally-carried genes into the host genome can occur. These features make AAV a candidate for use as a viral vector in gene therapy. However, certain AAV serotypes exhibit liver tropism, which, depending on the disease being treated, may be desirable or not.

It would be beneficial to understand how AAV liver tropism is determined and, based on that information, to be able to manipulate the tropism of AAV.

SUMMARY

Tissue specificity, i.e., tissue tropism, of AAV is determined by the capsid serotype, and the methods and compositions described herein enable one to alter the tissue tropism of a particular AAV with specificity to improve therapies delivered by these altered AAV. For example, altering or changing the liver tropism of an AAV can be beneficial, for example, when the liver is the desired target, e.g., by enhancing a natural liver tropism, and also when the liver is not the desired target, e.g., by reducing a natural liver tropism. For example, a lower dose of a given AAV can be administered to a subject when that virus is more effectively delivered to and more efficiently transfects cells in the liver (or a non-liver organ).

In one aspect, this disclosure provides methods of altering the tissue tropism of adeno-associated virus (AAV) vectors. Such methods typically include locating an amino acid position within an AAV capsid protein corresponding to position 266 in a capsid protein of Anc80 (SEQ ID NO:1); and replacing a naturally occurring amino acid at the located position with a glycine (G) amino acid residue to provide enhanced liver tropism of the resulting AAV vector, or with an alanine (A) amino acid residue to reduce liver tropism, i.e., provide liver de-targeting of the resulting AAV.

In some embodiments, such methods include replacing a naturally occurring amino acid at the located position with a G amino acid residue to provide enhanced liver tropism, e.g., liver enrichment, of the resulting AAV vector. In some embodiments, such methods include replacing the naturally occurring amino acid at the located position with an A amino acid residue to provide reduced liver tropism, e.g., de-targeting of the liver by the resulting AAV.

In another aspect, this disclosure provides methods of altering the tissue tropism of an adeno-associated virus (AAV) vectors. Such methods typically include locating an amino acid position within an AAV capsid protein corresponding to position 168 in a capsid protein of Anc80 (SEQ ID NO:1); and replacing a naturally occurring amino acid at the located position with an arginine (R) amino acid residue to provide enhanced liver tropism, e.g., liver enrichment, of the resulting AAV vector, or with a lysine (K) amino acid residue to provide reduced liver tropism, e.g., liver de-targeting of the resulting AAV.

In some embodiments, such methods include replacing the naturally occurring amino acid at the located position with an R amino acid residue to provide liver enrichment of the resulting AAV vector. In some embodiments, such a method can include replacing the naturally occurring amino acid at the located position with a K amino acid residue to provide reduced liver targeting of the resulting AAV.

In another aspect, methods of altering the tissue tropism of an adeno-associated virus (AAV) vector are provided. Such methods typically include locating a liver toggle region as defined in FIG. 14 within an AAV capsid protein; and replacing a naturally occurring liver toggle region with a liver toggle region from a heterologous serotype or de novo derived sequence to alter liver tropism, e.g., to provide enhanced or decreased liver targeting of the resulting AAV vector.

In some embodiments, when the heterologous or de novo derived liver toggle region comprises a G amino acid residue at a position within an AAV capsid protein corresponding to position 266 in a capsid protein of Anc80 (SEQ ID NO:1), liver enrichment of the resulting AAV vector is provided. In some embodiments, when the heterologous or de novo derived liver toggle region comprises an A amino acid residue at a position within an AAV capsid protein corresponding to position 266 in a capsid protein of Anc80 (SEQ ID NO:1), reduced liver targeting of the resulting AAV vector is provided.

In some embodiments, the replacing step is performed using site-directed mutagenesis, restriction digest and ligation of extant or de novo synthesized DNA, homology-mediated assembly of extant or de novo synthesized DNA, or combinations thereof. In some embodiments, the locating step is performed by sequencing.

In another aspect, the disclosure provides methods of screening for an AAV whose transfection into the liver is enriched or reduced. Such methods typically include sequencing a nucleic acid that encodes an AAV capsid protein; locating an amino acid position within the AAV capsid protein corresponding to position 266 in a capsid protein of Anc80 (SEQ ID NO:1); and identifying an AAV capsid protein having a G amino acid residue at the located position or an A amino acid residue at the located position. Generally, a G amino acid residue at the located position indicates an AAV whose transfection into the liver is enriched, while an A amino acid residue at the located position indicates an AAV whose transfection into the liver is reduced.

In another aspect, the disclosure provides methods of screening for an AAV whose transfection into the liver is enriched or reduced. Such methods typically include sequencing a nucleic acid that encodes an AAV capsid protein; locating an amino acid position within the AAV capsid protein corresponding to position 168 in a capsid protein of Anc80 (SEQ ID NO:1); and identifying an AAV capsid protein having an R amino acid residue at the located position or a K amino acid residue at the located position. Generally, an R amino acid residue at the located position indicates an AAV whose transfection into the liver is enriched, while an K amino acid residue at the located position indicates an AAV whose transfection into the liver is reduced.

In still another aspect, this disclosure provides an AAV having the sequence shown in SEQ ID NO:1 [Anc80], wherein $X_3$ at position 266 is selected from a G or an A.

In another aspect, this disclosure provides an AAV having the sequence shown in SEQ ID NO:1 [Anc80], wherein $X_1$ at position 168 is selected from an R or a K.

In another aspect, this disclosure provides an AAV that has the sequence shown in SEQ ID NO: 2 [Anc80L65].

In yet another aspect, this disclosure provides an AAV having the sequence shown in SEQ ID NO: 3 [Anc80L65 G266A].

In another aspect, this disclosure provides an AAV having the sequence shown in SEQ ID NO: 4 [AAV9 G267A].

In another aspect, this disclosure provides an AAV having the sequence shown in SEQ ID NO: 5 [AAV9 G267A S269T].

In still another aspect, this disclosure provides an AAV having the sequence shown in SEQ ID NO: 6 [AAV9 Anc80L65-VRI].

In another aspect, this disclosure provides an AAV having the sequence shown in SEQ ID NO: 7 [AAV9 Anc80L65 G266A-VRI].

In another aspect, this disclosure provides an AAV having the sequence shown in SEQ ID NO: 8 [AAV3B A266G].

In yet another aspect, this disclosure provides an AAV having the sequence shown in SEQ ID NO: 9 [AAV3B A266G S267 N268T].

In another aspect, this disclosure provides an AAV having the sequence shown in SEQ ID NO: 10 [AAV3B G265 A266A].

In still another aspect, this disclosure provides an AAV having the sequence shown in SEQ ID NO: 11 [AAV3B G265 A266G].

In another aspect, this disclosure provides an AAV having the sequence shown in SEQ ID NO: 12 AAV3B G265 A266A S268T].

In another aspect, this disclosure provides an AAV having the sequence shown in SEQ ID NO: 13 [AAV3B G265 A266G S268T].

In still another aspect, this disclosure provides an AAV having the sequence shown in SEQ ID NO: 14 [AAV3B AAV9-VRI].

In another aspect, this disclosure provides an AAV having the sequence shown in SEQ ID NO: 15 [AAV3B Anc80L65-VRI].

In yet another aspect, this disclosure provides an AAV having the sequence shown in SEQ ID NO: 16 [AAV3B Anc80L65 G266A-VRI].

In another aspect, this disclosure provides an AAV that has the sequence shown in SEQ ID NO: 17 [Anc80L65 R168K].

As used herein, "tissue tropism" refers to a natural tissue-specificity for infection and/or transfection of a cell by a particular AAV. For example, many AAV exhibit liver tropism, which means that these AAV preferentially infect and/or transfect liver cells rather than cells of other tissue types. Tissue tropisms are often based on specific surface proteins, e.g., receptor proteins, found on the surface of cells in a specific tissue and/or on the surface of specific AAV.

As used herein, "toggle" refers to a specific location or region within an AAV capsid protein associated with a tissue tropism of that AAV. Thus, when the naturally occurring amino acid at the toggle location or region as described herein is replaced with a different amino acid, the tissue tropism of that AAV is altered. Therefore, a "liver toggle," e.g., "liver toggle 1," refers to a residue that can be "switched" so that transfection occurs predominantly or essentially entirely into liver cells or predominantly or essentially entirely not into liver cells.

Also as used herein, "liver toggle region" refers to the 20 amino acid residues located between two beta-strands within which the "liver toggle" resides, as defined in FIG. 14. Therefore, a "liver toggle region" refers to a sequential series of residues that can be "switched" via import from heterologous AAVs or via de novo derivation so that transfection occurs predominantly or essentially entirely into liver cells or predominantly or essentially entirely not into liver cells. The liver toggle region overlaps with variable region I (VRI), so all toggle region swaps use this nomenclature as a shorthand.

As used herein, "toggle 2" refers to a switch independent of the "toggle 1." Therefore, "liver toggle 2" refers to another residue that is different than the residue at issue in liver toggle 1, and that can be "switched" so that transfection occurs predominantly or essentially entirely into liver cells or predominantly or essentially entirely not into liver cells.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1 is an Anc80 scaffold sequence (SEQ ID NO: 1) showing eleven positions that were varied to generate a $2^{11}$ (2048)-variant Anc80 library utilized for in vivo screening. Positions X1 and X3, highlighted, has been determined to be liver toggle positions, and correspond to residues 168 and 266 in the Anc80 capsid sequence. The residue at X3 is the dominant position defining whether the vector efficiently delivers genes to hepatocytes, and as such will be referred to as the "liver toggle" or "toggle." Position X1 is referred to herein as "toggle 2."

FIGS. 2A and 2B are the amino acid sequences of Anc80L65 (SEQ ID NO:2) and Anc80L65 G266A (SEQ ID NO:3), respectively. Both sequences are identical except for the liver toggle. The glycine (G)/alanine (A) liver toggle in both the nucleic acid and protein sequences are bolded and underlined.

FIGS. 3A and 3B are representations of the amino acid sequences of AAV9 G267A (SEQ ID NO:4) and AAV9 G267A S269T (SEQ ID NO:5), respectively. These sequences represent the identification and alteration of the liver toggle in AAV9, and an additional alteration in the latter to match the corresponding location in Anc80L65. The residues altered from AAV9 are bolded and underlined.

FIGS. 4A and 4B are representations of the amino acid sequences of AAV9 Anc80L65-VRI (SEQ ID NO:6) and AAV9 Anc80L65 G266A-VRI (SEQ ID NO:7), respectively. These sequences represent the importation of the liver toggle region, both liver enriching and liver de-targeting, from Anc80L65 into AAV9. The imported sequences are bolded and underlined.

FIGS. 5A and 5B are the sequences of AAV3B A266G (SEQ ID NO:8) and AAV3B A266G S267_N268T (SEQ ID NO:9), respectively. Though foreshortened compared to the Anc80 liver toggle region, making identification uncertain, A266 of AAV3B may represent the liver toggle in this serotype. AAV3B transduces murine livers poorly, suggesting that the alteration A266G may improve this function. The insertion of a T creates a liver toggle region with greater identity to Anc80. The residues altered from AAV3B or inserted are bolded and underlined.

FIGS. 6A and 6B are the sequences of AAV3B G265_A266A (SEQ ID NO:10) and AAV3B G265_A266G (SEQ ID NO:11), respectively. The liver toggle region of AAV3B is foreshortened compared to the Anc80 liver toggle region. Insertion of the liver-enriching G or liver-de-targeting A from the corresponding position in Anc80 may import this function. The residues altered from AAV3B or inserted are bolded and underlined.

FIGS. 7A and 7B are the sequences of AAV3B G265_A266A S268T (SEQ ID NO: 12) and AAV3B G265_A266G S268T (SEQ ID NO:13), respectively. The liver toggle region of AAV3B is foreshortened compared to the Anc80 liver toggle region. Insertion of the liver-enriching G or liver-de-targeting A from the corresponding position in Anc80 may import this function. Alteration of the S to T at position 268 creates a region with greater identity to Anc80. The residues altered from AAV3B or inserted are bolded and underlined.

FIGS. 8A, 8B and 8C are the sequences of AAV3B AAV9-VRI (SEQ ID NO:14), AAV3B Anc80L65-VRI (SEQ ID NO:15), and AAV3B Anc80L65 G266A-VRI (SEQ ID NO: 16), respectively. These sequences represent the importation of the liver toggle region, both liver enriching and liver de-targeting, from AAV9, Anc80L65, and Anc80L65 G266A into AAV3B. The imported sequences are bolded and underlined.

FIG. 15 is a table of Liver Toggle Region sequences (SEQ ID NOs: 40-55, top to bottom), oriented to the a-toggle (NDN) at the C-terminus, of Anc80L65, AAV3B, and AAV9 serotypes, as well as variants constructed to test the liver toggle hypothesis. The final two columns list the known "on" or "off" transduction efficiency in murine and primate liver of Anc80L65, AAV3B, and AAV9, and the in vivo results for variants reported herein, in bold. The efficiency predicted by the hypothesis for un-tested variants is indicated by italics.

FIG. 17 is a table that shows predictions of the liver transduction efficiency (similar to FIG. 15) of variants with "swapped" liver toggle regions (SEQ ID NOs: 56-63, top to bottom). The final two columns list in bold the in vivo determined "on" or "off" transduction efficiency in murine livers for these variants as reported herein. The efficiency predicted by the hypothesis for un-tested variants is indicated by italics.

FIG. 23 is the sequence Anc80L65 R266K (SEQ ID NO:17). The sequence is identical to Anc80L65 except for liver toggle 2. The arginine (R)/lysine (K) liver toggle is highlighted.

FIG. 25A represents on the left an MA plot showing the abundance of the 2048 Anc80 library members in murine hepatocytes, both C57BL/6 and FIG. 25B represents on the left an MA plot of a xenografted FRG mouse model, versus viral input at day 28. The variants that are enriched in these cells have been boxed, and identity of each of 11 toggle positions is indicated in the "heatmap" on the right in both figures. Of eleven toggled positions, the liver toggle position X3 correlates with enrichment. Position X1 Toggle 2, state 1, also correlates with enrichment, markedly so with the most enriched variants.

DETAILED DESCRIPTION

Figure 9:
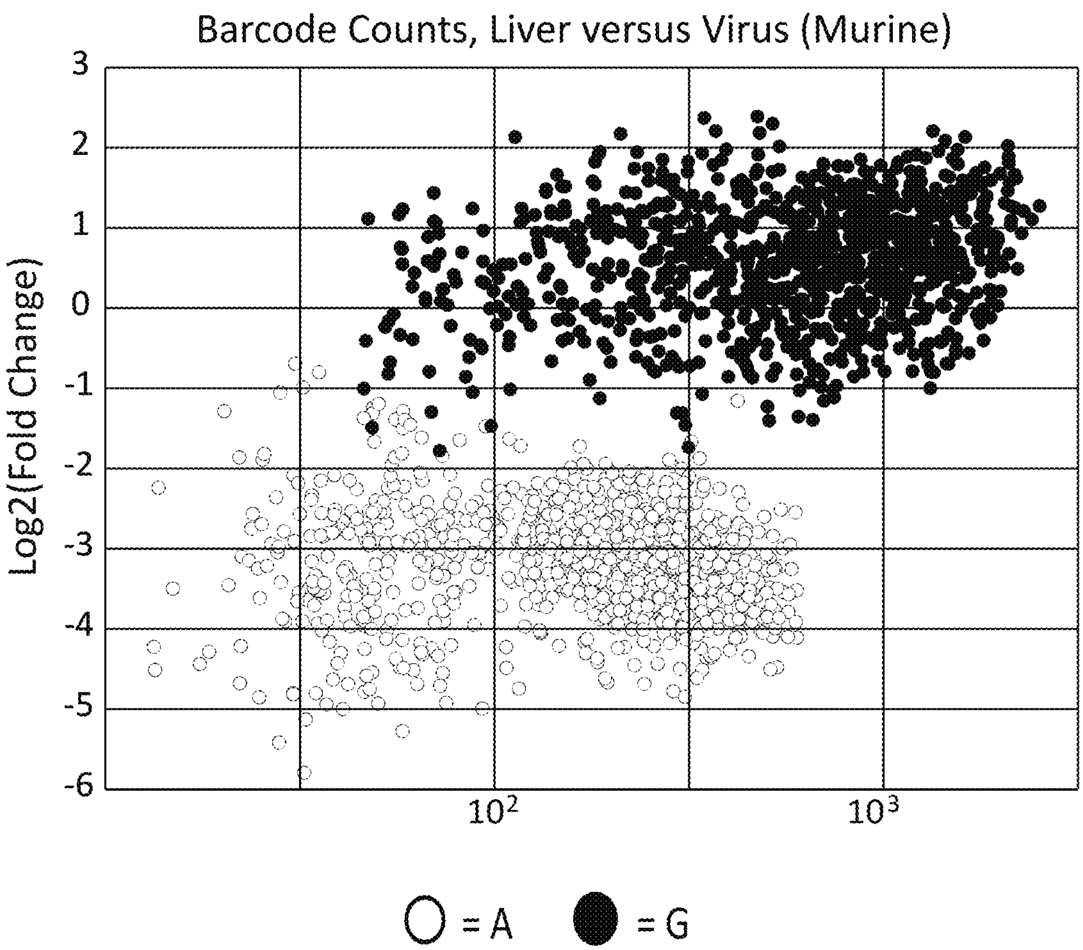
FIG. 9 is an MA plot showing the abundance of the 2048 Anc80 library members in liver versus viral input in C57/BL6J mice. On the y-axis, zero indicates no change from the input, with positive and negative values indicating relative enrichment or de-targeting, respectively. Of eleven toggled positions, position X3 correlates with the bimodality observed.

Adeno-associated virus (AAV) is primarily liver-tropic. Whereas this tropism is a benefit to gene therapy treatments for diseases that have a liver etiology, the number of genome-containing viral particles required to transduce this organ effectively nevertheless can present a burden to both patient and provider. Related, but contrasting, treatment of diseases with a non-liver etiology may be less effective, or require higher dosing, because the liver acts as a sink for most of the therapeutic material delivered by AAV. In addition, promising AAV serotypes do not transduce murine livers efficiently, severely limiting the use of mouse models for clinical relevance and dosing studies.

Previous approaches to identify AAV sequences correlated with tropism have relied, for example, upon the comparison of highly related extant serotypes with distinct characteristics, random domain swaps between unrelated serotypes, or consideration of higher-order structure, to identify motifs that define liver tropism. For example, mapping determinants of AAV tropism have been carried out by comparing highly related serotypes. One such example is the single-amino acid change (E531K) between AAV1 and AAV6 that improves murine liver transduction in AAV1 (Wu et al., 2006, J. Virol., 80 (22): 11393-7). Another example is a reciprocal domain swap between AAV2 and AAV8 that altered tropism, but failed to define any robust specific tissue-targeting motifs (Raupp et al., 2012, J. Virol., 86 (17): 9396-408). Further, global consideration of structure has only highlighted gross differences between better- or worse-liver-transducers that are more observational than useful in practice (Nam et al., 2007, J. Virol., 81 (22): 12260-71).

Identification of Liver Toggles in the AAV Capsid Protein

This disclosure describes the screening of a rationally-designed AAV capsid library to identify an amino acid change at a single site that results in bimodal murine liver tropism (e.g., a "liver toggle"). This disclosure also describes a specific residue in an AAV capsid that a) improves liver transduction in humans, or de-targets the liver, if desired, thereby allowing the effective dose to be reduced, and b) improves murine liver transduction while minimally altering other favorable characteristics, allowing these serotypes to be used in murine disease models.

As described herein, the liver-specific tropism of an AAV capsid protein can be altered by changing one residue at position 266 in Anc80 (SEQ ID NO:1). For example, changing a non-glycine (G) amino acid residue to a glycine (G) amino acid residue at this position results in enhanced or increased tropism or targeting of the AAV to the liver; alternately, changing a non-alanine (A) amino acid residue to an alanine (A) amino acid residue at this position results in reduced tropism or targeting of the AAV to the liver ("de-targeting"). Thus, the propensity of an AAV to infect and/or transfect the liver can be increased by changing a non-G residue at position 266 within the AAV capsid protein of Anc80 (SEQ ID NO:1) to a G residue, whereas the propensity of an AAV to infect and/or transfect the liver can be reduced by changing a non-A residue at position 266 within the AAV capsid protein of Anc80 (SEQ ID NO:1) to an A residue.

In some embodiments, an amino acid position corresponding to position 266 in Anc80 in other known capsid proteins from, for example, AAV serotype 1, 2, 3, 4, 5, 6, 7, 8, 9, 10, or 11, can be changed to either a G amino acid residue or an A amino acid residue depending upon the liver-specific tropism that is desired. In some embodiments, insertion of either a G amino acid residue or an A amino acid residue can alter the liver-specific tropism as desired. In some embodiments, additional alterations, insertions, or deletions in the liver toggle region can enhance liver-specific tropism as desired. In some embodiments, the entire native liver toggle region, containing the toggle residue, can be replaced with that of a heterologous capsid or de novo synthesized sequence to achieve the desired enhanced or reduced liver tropism.

In some embodiments, capsid proteins can be genetically engineered or designed to have the desired amino acid residue corresponding to position 266 in Anc80 (SEQ ID NO: 1) such that, when combined with other viral components and assembled into AAV viral particles, the AAV viral particles are enriched in the liver or de-targeted to the liver (compared to, e.g., the capsid sequence prior to being changed, or a corresponding capsid sequence not having a G or not having an A at the relevant position, or a corresponding capsid sequence having an A instead of a G or a G instead of an A at the relevant position).

As described herein, the liver tropism of an AAV capsid protein can also be altered by changing one residue at position 168 in Anc80 (SEQ ID NO:1). For example, changing a non-arginine amino acid residue to an arginine (R) amino acid residue at this position results in enhanced or increased liver tropism of the AAV; alternatively, changing a non-lysine amino acid residue to a lysine (K) amino acid residue at this position results in reduced liver tropism of the AAV ("de-targeting"). Thus, the propensity of an AAV to infect and/or transfect the liver can be increased or enhanced by changing a non-R residue at position 168 within the AAV capsid protein of Anc80 (SEQ ID NO:1) to an R residue, whereas the propensity of an AAV to infect and/or transfect the liver can be reduced by changing a non-K residue at position 168 within the AAV capsid protein of Anc80 (SEQ ID NO: 1) to a K residue.

In some embodiments, an amino acid position corresponding to position 168 in Anc80 in other known capsid proteins from, for example, AAV serotype 1, 2, 3, 4, 5, 6, 7, 8, 9, 10, or 11, can be changed to either an R amino acid residue or a K amino acid residue depending upon the liver-specific tropism that is desired.

It would be understood that amino acids with similar properties (e.g., polarity, acidity/basicity, hydrophobicity, charge, and/or size) to the tropism-imparting amino acids described herein could be used (e.g., instead of the G or A at position 266 relative to Anc80 or instead of the R or K at position 168 relative to Anc80).

Figure 14:
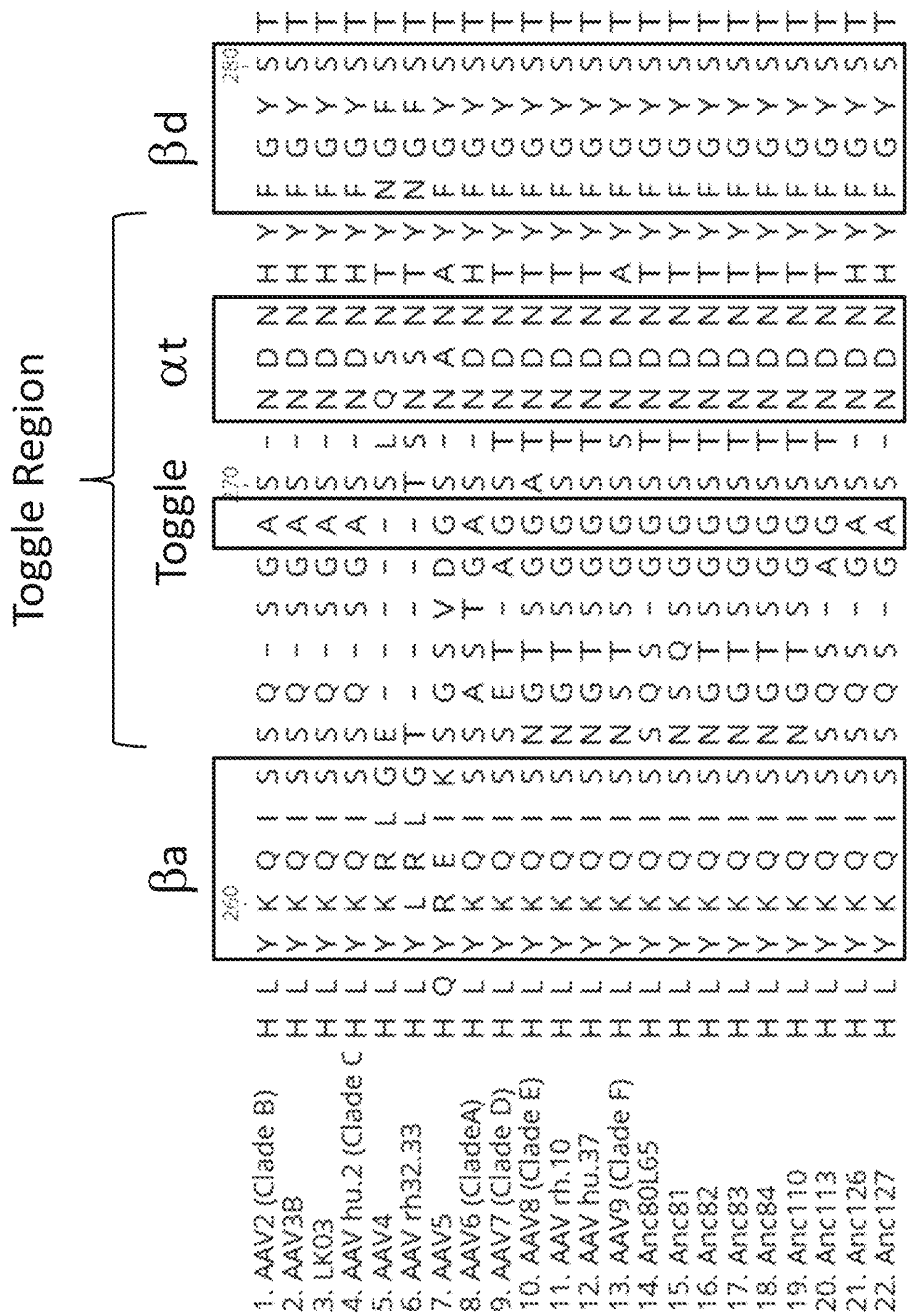
FIG. 14 is a sequence alignment of archetypes of AAV clades and clones (e.g., rows 1, 4, 8-10 and 13), clinically relevant serotypes of AAV (both naturally-occurring and engineered; e.g., rows 2, 3, 5-7, 11, and 12), and Anc variants (e.g., rows 14-22). Rows 1-22 correspond to SEQ ID NOs: 18-39. The location of b-ascending (ba), b-descending (bd), a-toggle (at), the Toggle Region, and the toggle position itself are indicated. b-ascending (ba) initiates at a conserved tyrosine, b-descending (bd) terminates at a conserved serine. The toggle represents residue 266 in Anc80L65, 267 in AAV9, and 257 in AAV5, emphasizing that position number is relative when defining the toggle.

As described herein, the liver-specific tropism of an AAV capsid protein can be altered by changing additional residues within the liver toggle region (as defined in FIG. 14). In some embodiments, a naturally occurring liver toggle region can be replaced with a liver toggle region from a heterologous serotype to have the desired liver tropism (e.g., to enhance liver tropism or reduce liver tropism of the resulting AAV vector). In some embodiments, a naturally occurring liver toggle region can be synthesized de novo to have the desired liver tropism (e.g., to enhance liver tropism or reduce liver tropism of the resulting AAV vector). As described herein, when the heterologous or de novo derived liver toggle region contains a G amino acid residue at a position within an AAV capsid protein corresponding to position 266 in a capsid protein of Anc80 (SEQ ID NO:1), liver tropism of the resulting AAV vector is enhanced, and when the heterologous or de novo derived liver toggle region contains an A amino acid residue at a position within an AAV capsid protein corresponding to position 266 in a capsid protein of Anc80 (SEQ ID NO: 1), liver tropism of the resulting AAV vector is reduced.

Based on the discoveries reported herein, it is clear that AAVs can be screened for those that are enriched in liver cells or de-targeted from liver cells based on the sequence of the capsid protein and, specifically, the sequence of the nucleic acid that encodes the amino acid residue that corresponds to positions 266 and/or 168 in Anc80 (SEQ ID NO: 1). Methods of sequencing nucleic acids are well known in the art and include, without limitation, chain terminating methods (e.g., the Sanger sequencing method) or chemical degradation methods (e.g., the Maxam-Gilbert sequencing method). Many variations and improvements have been developed and are used in the art for sequencing, including automated sequencing methods and high-throughput sequencing methods.

As used herein, enriched or enrichment refers to an increase in the number of AAV genomes in liver cells compared to the number of AAV genomes in liver cells when the capsid protein does not have a G amino acid residue at an amino acid position corresponding to position 266, and/or an R amino acid position corresponding to position 168, in Anc80 (SEQ ID NO:1) (e.g., the original or wild type sequence, or the sequence prior to being changed). As used herein, de-targeted or de-targeting refers to a decrease in the number of AAV genomes in liver cells compared to the number of AAV genomes in liver cells when the capsid protein does not have an A amino acid residue at an amino acid position corresponding to position 266, and/or a K amino acid position corresponding to position 168, in Anc80 (SEQ ID NO:1) (e.g., the original or wild type sequence, or the sequence prior to being changed).

Methods of screening for the number of AAV genomes in the liver are known in the art and typically include in vitro transduction of immortalized and/or primary hepatocytes as well as in vivo systemic injections of both wild type and humanized mice (see, for example, Grimm et al., 2008, J. Virol., 82:5887-911; Lisowski et al., 2014, Nature, 382: doi: 10.1038/nature12875).

Representative capsid proteins that impart efficient (or enhanced) liver tropism or inefficient (or reduced) liver tropism are provided herein. The sequences of representative capsid proteins that impart efficient liver tropism (e.g., that results in an enrichment of AAV genomes in the liver cells) is shown in SEQ ID NO: 2 [AAV9 Anc80+266G], SEQ ID NO: 6 [AAV9 Anc80+266G VRI], SEQ ID NO: 9 [AAV3B A266G S267 N268T], SEQ ID NO: 11 [AAV3B G265 A266G], SEQ ID NO: 13 [AAV3B G265 A266G S268T], SEQ ID NO: 14 [AAV3B AAV9+267G-VRI], SEQ ID NO: 15 [AAV3B Anc80+266G-VRI], whereas the sequences of representative capsid proteins that impart a reduced liver tropism (e.g., that results in a de-targeting of AAV particles to the liver) is shown in SEQ ID NO: 3 [Anc80+266A], SEQ ID NO: 4 [AAV9 G267A], SEQ ID NO: 5 [AAV9 G267A S269T], SEQ ID NO: 7 [AAV9 Anc80+266A-VRI], SEQ ID NO: 10 [AAV3B G265 A266A], SEQ ID NO: 12 [AAV3B G265 A266A S268T], SEQ ID NO: 16 [AAV3B Anc80+266A-VRI], SEQ ID NO: 17 [Anc80L65 R168K].

As explained in more detail below, the sequences of the two AAV capsid proteins that exhibit the bi-modal pattern of liver transduction, SEQ ID NO:2 and SEQ ID NO:3, originated from an Anc80 scaffold sequence having the sequence shown in SEQ ID NO:1, where position 266, shown with an X3 in FIG. 1, is either a G or an A. Similarly, the sequences of the two AAV capsid proteins that exhibit the bi-modal pattern of liver transduction, SEQ ID NO:16 and SEQ ID NO:17, originating from an Anc80 scaffold sequence having the sequence shown in SEQ ID NO:1, where position 168, shown with an X1, is either an R or a K.

Nucleic Acids Encoding an AAV Capsid Protein Containing a Liver Toggle

As described herein, changing or inserting an amino acid residue in the AAV capsid protein between a G amino acid residue and an A amino acid residue at position 266 toggles the liver tropism of the resulting AAV between enrichment and de-targeting. Similarly, changing the amino acid residue in the AAV capsid protein between an R amino acid residue and a K amino acid residue at position 168 toggles liver tropism of the resulting AAV between enrichment and de-targeting. Changes to a sequence typically are made at the nucleic acid level, and the changes are translated into the encoded amino acid sequence (e.g., the encoded protein). As used herein, nucleic acids can include DNA and RNA, including those that contain one or more nucleotide analogs or backbone modifications. A nucleic acid can be single-stranded or double-stranded, which usually depends upon its intended use.

Changes can be introduced into nucleic acids using various methods, many of which are well known in the art. For example, changes can be introduced into nucleic acids using mutagenesis (e.g., site-directed mutagenesis, PCR-mediated mutagenesis) or by chemically synthesizing the nucleic acid molecule including the desired change(s). Sec, for example, Sambrook, Fritsch & Maniatis (*Molecular Cloning: a laboratory manual,* 1989, Ed. 2), and Dieffenbach & Dveksler (*PCR primer: a laboratory manual,* 2003, Ed. 2).

Nucleic acids can be obtained (e.g., isolated) using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

An "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

Polypeptides can be obtained (e.g., purified) from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

Nucleic acids can be propagated within a vector. Vectors can include viral vectors or non-viral vectors, and also can include expression vectors. Many vectors are commercially available, and vectors can be readily produced using recombinant DNA techniques routine in the art. A vector containing a nucleic acid can have expression elements, which, in some instances, can be operably linked to such a nucleic acid. Vectors further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)).

Expression elements are known in the art and include nucleic acid sequences that direct and regulate expression of coding sequences. One example of an expression element is a promoter sequence. Expression elements also can include introns, enhancer sequences, response elements, or inducible elements that modulate expression of a nucleic acid. Expression elements can be of viral origin, or for non-viral molecular biology techniques (e.g., simple growth of a plasmid vector), expression elements can be, without limitation, of bacterial, yeast, insect, or mammalian origin, or expression elements can be a combination of elements from different origins. As used herein, operably linked means that a promoter or other expression element(s) are positioned in a vector relative to a nucleic acid in such a way as to direct or regulate expression of the nucleic acid. In some instances, operably linked means that two sequences are in-frame.

Methods of introducing a viral vector into a host cell are known in the art, and typically take advantage of the virus's natural ability for infection. Methods of introducing a non-viral vector into a host cell are known in the art. As used herein, "host cell" refers to the particular cell into which the viral or non-viral vector is introduced and also includes the progeny or potential progeny of such a cell. A host cell can be a prokaryotic or eukaryotic cell as appropriate. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art. Non-viral nucleic acids can be introduced into host cells, either in vivo and in vitro, using known methods such as, without limitation, electroporation, calcium phosphate precipitation, polyethylene glycol (PEG) transformation, heat shock, lipofection, microinjection, and viral-mediated nucleic acid transfer.

Methods of Using an AAV Capsid Protein Containing a Liver Toggle

An AAV virus can include a transgene (in cis or trans with other viral sequences) for delivery to a cell. A transgene can be, for example, a reporter gene (e.g., beta-lactamase, beta-galactosidase (LacZ), alkaline phosphatase, thymidine kinase, green fluorescent polypeptide (GFP), chloramphenicol acetyltransferase (CAT), or luciferase, or fusion polypeptides that include an antigen tag domain such as hemagglutinin or Myc) or a therapeutic gene (e.g., genes encoding hormones or receptors thereof, growth factors or receptors thereof, differentiation factors or receptors thereof, immune system regulators (e.g., cytokines and interleukins) or receptors thereof, enzymes, RNAs (e.g., inhibitory RNAs or catalytic RNAs), or target antigens (e.g., oncogenic antigens, autoimmune antigens)).

The particular therapeutic gene will depend, at least in part, on the particular disease or deficiency being treated. Simply by way of example, gene transfer or gene therapy can be applied to the treatment of hemophilia, retinitis pigmentosa, cystic fibrosis, leber congenital amaurosis, lysosomal storage disorders, inborn errors of metabolism (e.g., inborn errors of amino acid metabolism including phenylketonuria, inborn errors of organic acid metabolism including propionic academia, inborn errors of fatty acid metabolism including medium-chain acyl-CoA dehydrogenase deficiency (MCAD)), cancer, achromatopsia, cone-rod dystrophies, macular degenerations (e.g., age-related macular degeneration), lipopolypeptide lipase deficiency, familial hypercholesterolemia, spinal muscular atrophy, Duchenne's muscular dystrophy, Alzheimer's disease, Parkinson's disease, obesity, inflammatory bowel disorder, diabetes, congestive heart failure, hypercholesterolemia, hearing loss, coronary heart disease, familial renal amyloidosis, Marfan's syndrome, fatal familial insomnia, Creutzfeldt-Jakob disease, sickle-cell disease, Huntington's disease, fronto-temporal lobar degeneration, Usher syndrome, lactose intolerance, lipid storage disorders (e.g., Niemann-Pick disease, type C), Batten disease, choroideremia, glycogen storage disease type II (Pompe disease), ataxia telangiectasia (Louis-Bar syndrome), congenital hypothyroidism, severe combined immunodeficiency (SCID), and/or amyotrophic lateral sclerosis (ALS). Also by way of example, gene transfer or gene therapy can be applied to the treatment of retinal dystrophy (e.g., (LUXTURNA™) (voretigene neparvovec-rzyl), which is a one-time gene therapy product indicated for the treatment of patients with confirmed biallelic RPE65 mutation-associated retinal dystrophy (Spark Therapeutics Inc., Philadelphia, PA)).

A therapeutic gene also can be, for example, an immunogen that is useful for immunizing a subject (e.g., a human, an animal (e.g., a companion animal, a farm animal, an endangered animal). For example, immunogens can be obtained from an organism (e.g., a pathogenic organism) or an immunogenic portion or component thereof (e.g., a toxin polypeptide or a by-product thereof). By way of example, pathogenic organisms from which immunogenic polypeptides can be obtained include viruses (e.g., picornavirus, enteroviruses, orthomyxovirus, reovirus, retrovirus), prokaryotes (e.g., Pneumococci, Staphylococci, Listeria, Pseudomonas), and eukaryotes (e.g., amebiasis, malaria, leishmaniasis, nematodes). It would be understood that the methods described herein and compositions produced by such methods are not to be limited by any particular transgene.

An AAV virus, usually suspended in a physiologically compatible carrier, can be administered to a subject (e.g., a human or non-human mammal) using standard techniques. Suitable carriers include saline, which may be formulated with a variety of buffering solutions (e.g., phosphate buffered saline), lactose, sucrose, calcium phosphate, gelatin, dextran, agar, pectin, and water. The AAV virus is administered in sufficient amounts to transduce or infect the relevant cells and to provide sufficient levels of gene transfer and expression to provide a therapeutic benefit without undue adverse effects. Conventional and pharmaceutically acceptable routes of administration include, but are not limited to, direct delivery to an organ such as, for example, the liver or lung, orally, intranasally, intra-tracheally, by inhalation, intravenously, intramuscularly, intraocularly, subcutaneously, intradermally, transmucosally, or by other routes of administration. Routes of administration can be combined, if desired.

The dose of the AAV virus administered to a subject will depend primarily on factors such as the condition being treated, and the age, weight, and health of the subject. For example, a therapeutically effective dosage of an AAV virus to be administered to a human subject generally is in the range of from about 0.1 ml to about 10 ml of a solution containing concentrations of from about $1\times10^{1}$ to $1\times10^{12}$ genome copies (GCs) of viruses (e.g., about $1\times10^{3}$ to $1\times10^{9}$ GCs). Transduction and/or expression of a transgene can be monitored at various time points following administration by DNA, RNA, or protein assays. In some instances, the levels of expression of the transgene can be monitored to determine the frequency and/or amount of dosage. Dosage regimens similar to those described for therapeutic purposes also may be utilized for immunization.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Materials and Methods for Identifying an AAV Liver Toggle

A $2^{11}$ (2048)-variant Anc80 library of AAV sequences (see, for example, U.S. Pat. No. 9,695,220) was generated by varying the eleven positions ($X_1$ to $X_{11}$ in FIG. 1) within the Anc80 scaffold sequence (SEQ ID NO: 1; FIG. 1). Each variant was cloned into a mammalian expression plasmid and transfected into HEK293 cells, with pRep and pAd Helper accessory plasmids, to produce the library in viral vector form. This library then was used for in vivo screening of liver localization (e.g., enrichment vs. de-targeting). Briefly, in one experiment three mice were injected with 2.7311 total gc (~1e13 gc/kg) with the Anc80 vector library. At day 3 post-injection, the mice were sacrificed and livers harvested and frozen. In another experiment, two rhesus macaques were injected with 1.6e12 gc/kg of the Anc80 vector library, with study termination and liver harvest occurring at day 28 post-injection. Total genomic DNA was extracted from the livers, and the population of viral variants present in the tissue was quantified by next generation sequencing. As described below, position $X_3$, highlighted in the Anc80 scaffold sequence shown in FIG. 1, was determined to be a liver toggle position. Position $X_3$ corresponds to residue 266 in the Anc80 scaffold sequence.

Figure 10:
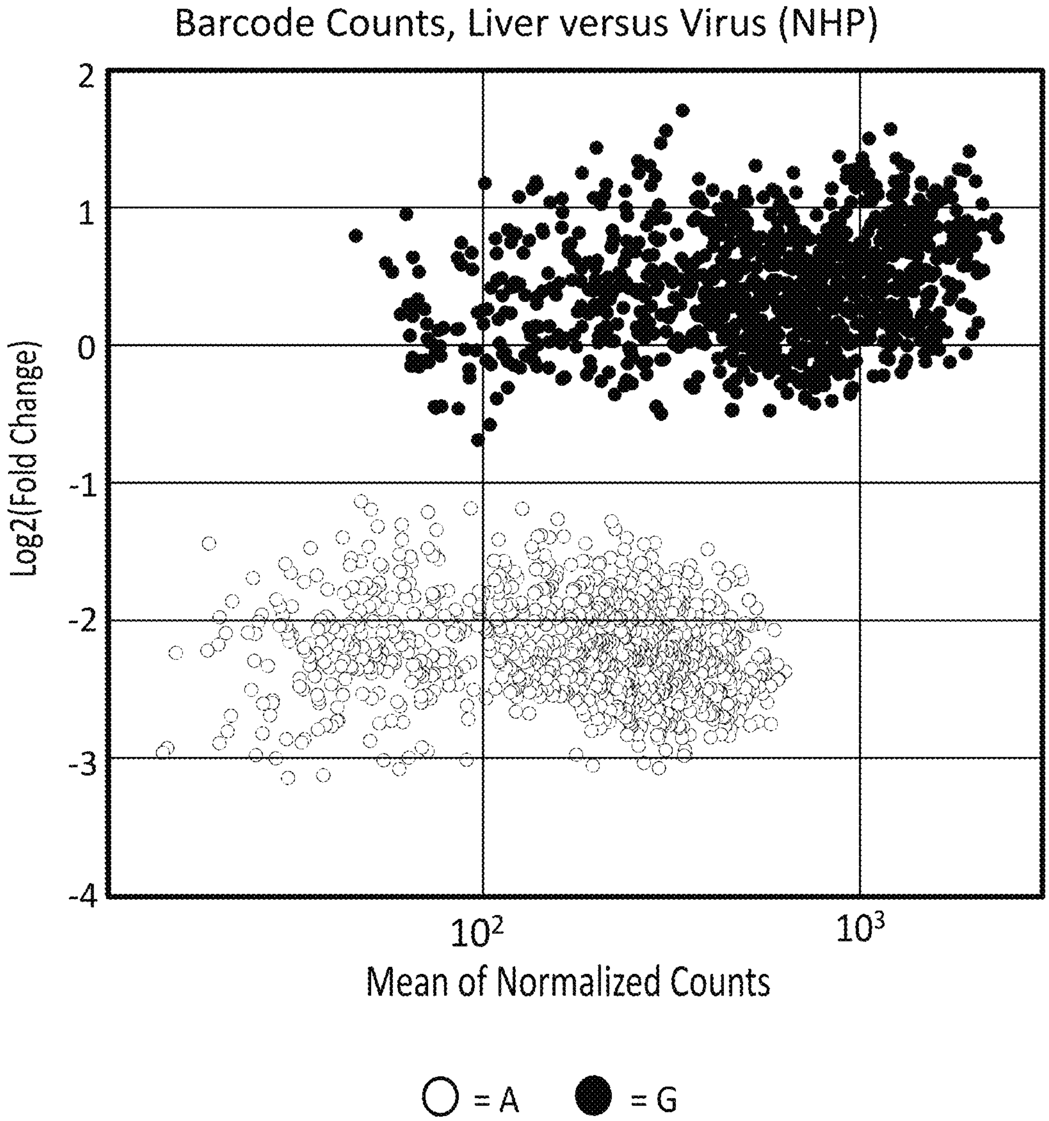
FIG. 10 is an MA plot showing the abundance of the 2048 Anc80 library members in liver versus viral input in the non-human primate rhesus macaque. On the y-axis, zero indicates no change from the input, with positive and negative values indicating relative enrichment or de-targeting, respectively. As with the murine liver, of eleven toggled positions, position X3 correlates with the bimodality observed.

The results of the in vivo screening experiments are shown in FIG. 9 and FIG. 10. A plot showing the abundance of the 2048-variant Anc80 library members in liver (y-axis) relative to viral input (x-axis) is shown. On the y-axis, zero indicates no change from the input, with positive and negative values indicating relative enrichment or de-targeting, respectively. Of the eleven toggled positions within the Anc80 scaffold sequence, position X3 correlated with the liver bimodality observed.

Subordinate but nonetheless relevant to liver enrichment or de-targeting is the identity of the amino acid residue at position X1, corresponding to residue 168 in the Anc80 scaffold sequence. A methodology called a toggle "heatmap" allowed for the consideration of every toggle position's identity in a visual format, and, by selecting groups of variants by a desired characteristic, a heatmap can reveal multiple toggle positions of influence, if present. Using the same data from FIG. 9 and FIG. 10, both wild-type C57BL/6 mice (FIG. 25) and rhesus macaques (FIG. 26) have the X3=1 (G) and X1=1 (R) present in the most-liver-enriched Anc80 variants. Supporting the relevance of position X1, a similar pattern was observed for both murine and human hepatocytes harvested from the FRG human liver xenotransplantation mouse model, as well as in primary human hepatocytes cultured in conditions that mimic in vivo liver architecture (micro patterned co-culture, MPCC).

Example 2

Generating and Testing an AAV Liver Toggle

Specific sequences from the 2048-variant Anc80 library (see, for example, U.S. Pat. No. 9,719,070, which is incorporated herein by reference in its entirety) containing the liver toggle were generated (FIG. 2). Anc80L65 (SEQ ID NO: 2) contains a G at position 266 and shows liver enrichment, and Anc80L65 G266A (SEQ ID NO: 3) contains an A at position 266 and shows liver de-targeting. The G/A liver toggle is highlighted and color-coded in FIG. 3 to be consistent with the color-coding shown in FIG. 2.

Each individual variant is derived by either site-directed mutagenesis or isothermal (Gibson) cloning combining PCR-generated and gene-synthesized fragments. These variants are cloned into a standard rep/cap "trans" plasmid for vector production. Vector variants expressing GFP and alpha-1-antityrpin then are produced by the Gene Transfer Vector Core at the Grousbeck Gene Therapy Center.

Figure 11:
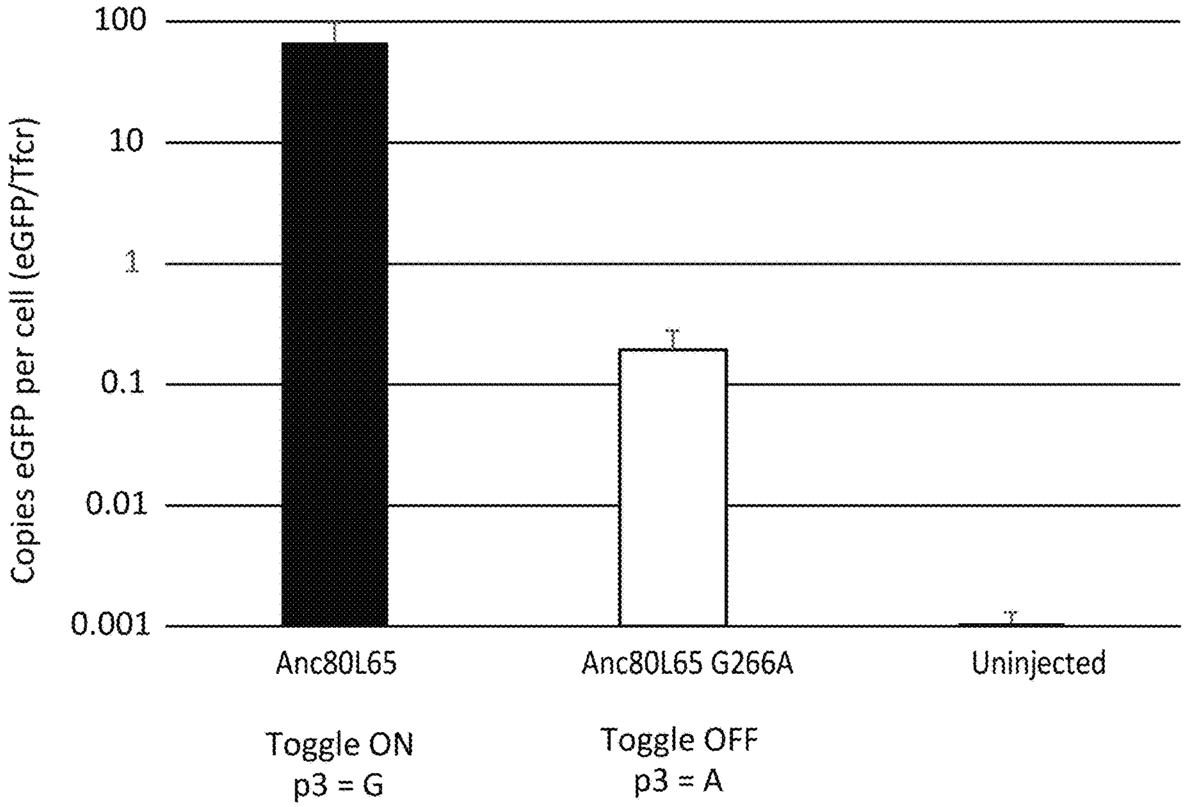
FIG. 11 is a bar graph that illustrates the clonal validation of the Anc80 liver toggle in murine livers. Both Anc80L65 (SEQ ID NO:2) and Anc80L65 G266A (SEQ ID NO: 3) were produced by triple transfection with the eGFP-expressing genome CB7.CI.eGFP.FF2A.hA1AT.RGB. These vectors were injected into 5 mice each at a dose of 1.25e12 gc/kg, and the mice were sacrificed three days later. Biodistribution of the recovered livers revealed a 100× enrichment in eGFP-encoding genomes per cell in the Anc80L65 toggle "on" vector versus the Anc80L65 G266A toggle "off" vector.
Figures 12A, 12B, 12C, 12D, 12E, 12F, 12G, 12H, 12I, 12J, 12K:
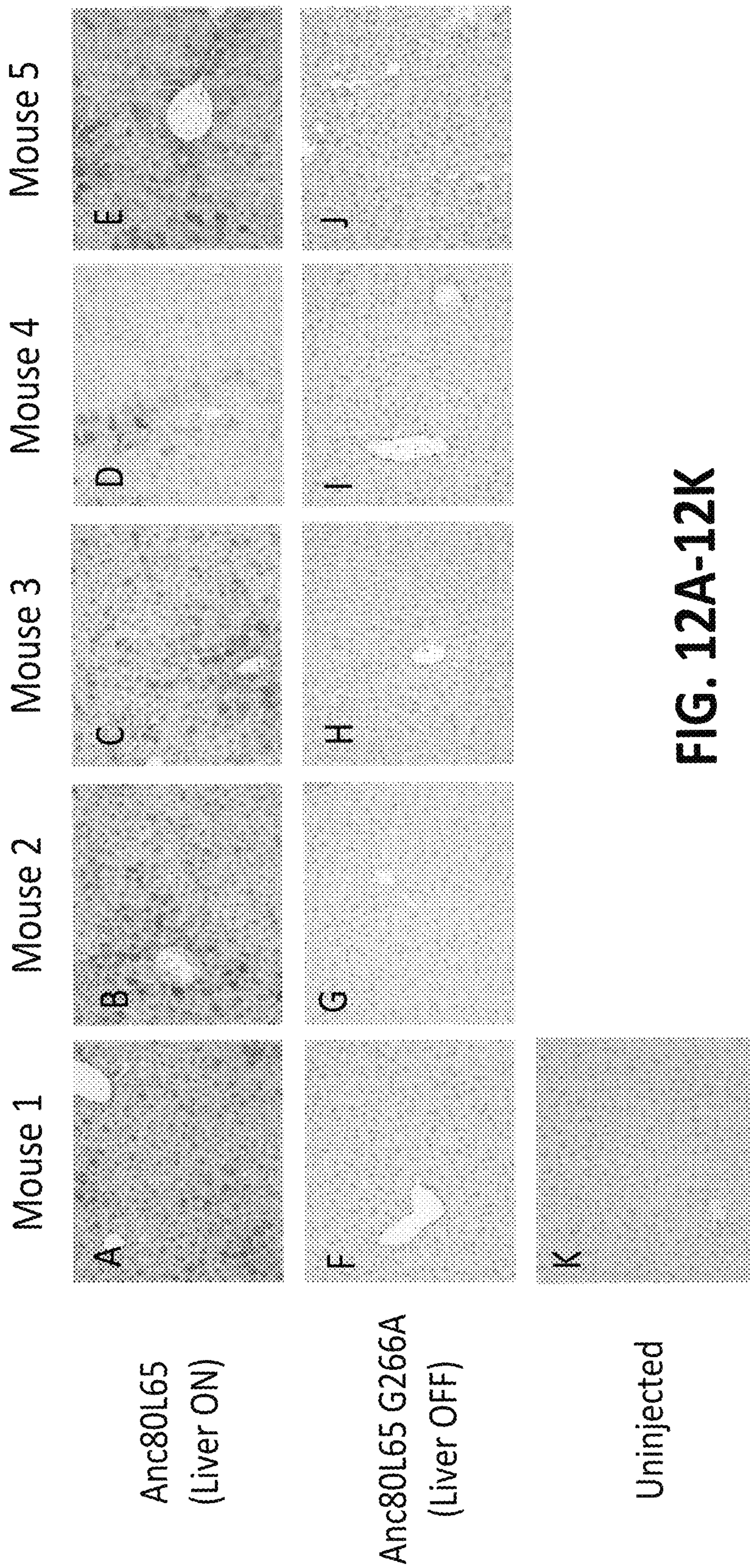
FIGS. 12A-12K are a series of 11 microscope images that illustrates the results of staining for eGFP in the livers of the 10 mice plus one un-injected control mouse from FIG. 11. There is markedly more eGFP staining in the livers of mice in injected with the Anc80L65 toggle "on" vector versus the Anc80L65 G266A toggle "off" vector.

Three 8-week old male mice per variant and parental control are injected with 1e11 total genome copies (~5e12 gc/kg), and liver tissue is harvest at day 3. The number of genome copies in the liver is determined by qPCR, and expressed as an absolute value and as a ratio to the parental control. FIG. 11 shows that Anc80L65 (SEQ ID NO: 2), containing a G at position 266, shows liver enrichment, and Anc80L65 G266A (SEQ ID NO: 3), containing an A at position 266, shows liver de-targeting. Further, FIG. 12 shows that expression from the genome, as observed by eGFP staining of liver tissue, is more evident when utilizing Anc80L65 (SEQ ID NO: 2) containing a G at position 266 versus Anc80L65 G266A (SEQ ID NO: 3) containing an A at position 266.

Example 3

Identify Comparable Liver Toggle Residues in Other Serotypes

Figure 13A:
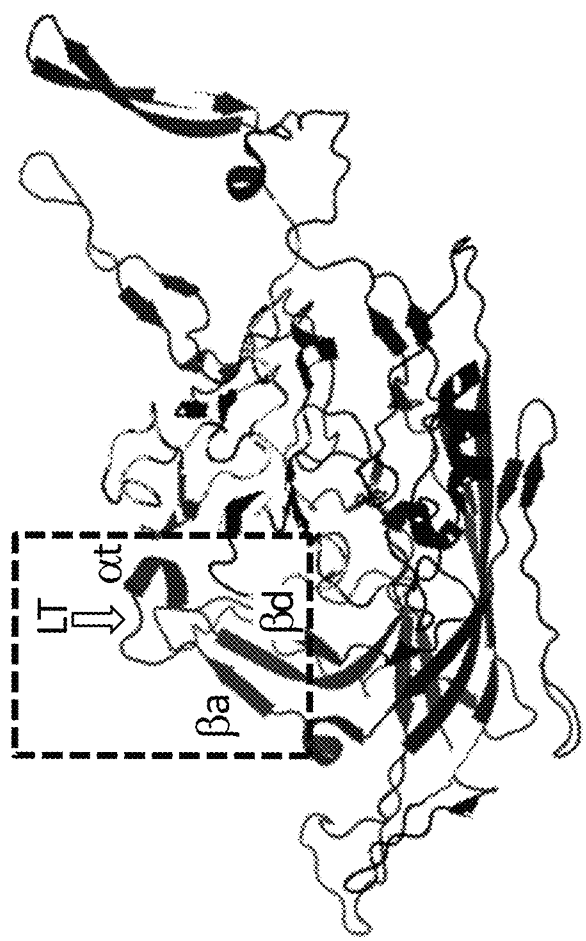
FIG. 13A is a schematic representation of the crystal structure of Adeno-associated virus 2 (AAV2) VP3 capsid monomer. The liver toggle ("LT") location is indicated by the arrow, and the structure of the region encompassing the LT is boxed.
Figure 13B:
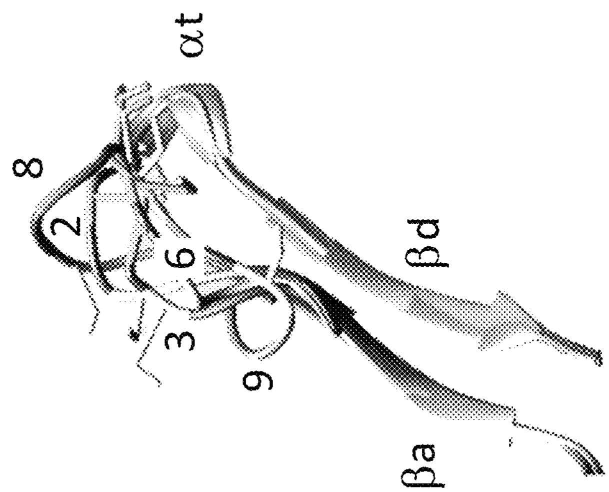
FIG. 13B is a schematic representation of a crystal structure showing an overlay of the LT regions from AAVs 2, 3, 6, 8, and 9, highlighting the local secondary structure that defines the toggle location. The Toggle Region is defined as the residues located between and including secondary structures β-ascending (βa) and β-descending (βd), with primary functionality encoded two to three residues N-terminal to α-toggle (αt). The LT residue is located within VR1, a beta-sheet-bounded loop, N-terminal to a three-residue alpha-helix.

FIG. 13A shows the crystal structure of AAV2 VP3 capsid monomer. The liver toggle ("LT") location is indicated by the arrow, and the structure of the region encompassing the LT is boxed. The liver toggle residue can be located 2-3 residues n-terminal to the □-toggle at a position comparable to position 266 of Anc80. FIG. 13B is the crystal structure of AAV2 VP3 showing an overlay of the LT regions from AAVs 2, 3, 6, 8, and 9 VP3s, highlighting the local secondary structure that defines the toggle location. The toggle region is defined as the residues located between and including secondary structures β-ascending (βa) and β-descending (βd), with primary functionality encoded two to three residues N-terminal to α-toggle (αt). The LT residue is located within VR1, a beta-sheet-bounded loop, N-terminal to a three-residue alpha-helix FIG. 14 is an alignment of primary VRI amino acid sequences from archetypal and clinically-relevant serotypes that encompass the liver toggle, with Anc80L65 located at line 15. The location of β-ascending (βa), β-descending (βd), α-toggle (αt), the Toggle Region, and the toggle itself are highlighted. β-ascending (βa) initiates at a conserved tyrosine, β-descending (βd) terminates at a conserved serine. For many serotypes, the position comparable to Anc80 266 can be readily inferred by close identity. In others, notably the clade B viruses AAV2 and AAV3, and the related viruses AAV4 and Rh32.33, the comparable position is more ambiguous or less evident. Nonetheless, primary sequence can serve as a guide to identify the liver toggle in other serotypes. As shown in FIG. 5, the toggle represents residue 266 in Anc80L65, residue 267 in AAV9, and residue 257 in AAV5, emphasizing that position number is relative when defining the toggle.

Example 4

Generating and Testing the AAV Liver Toggle in Other Serotypes

Similarly, FIG. 15 is a sequence alignment of the Liver Toggle Regions, oriented to the α-toggle (NDN) at the C-terminus, of Anc80L65, AAV3B, and AAV9 serotypes, as well as variants constructed to test the liver toggle hypothesis. Anc80L65, AAV3B, and AAV9, and other variants have been tested in murine (M) or primate (P) livers in vivo and murine liver transduction efficiencies for these serotypes is indicated by an "on" or "off" in the two final columns. The phenotype for completed experiments is indicated in bold; the phenotype for experiments still in progress are indicated in italics.

Figure 16:
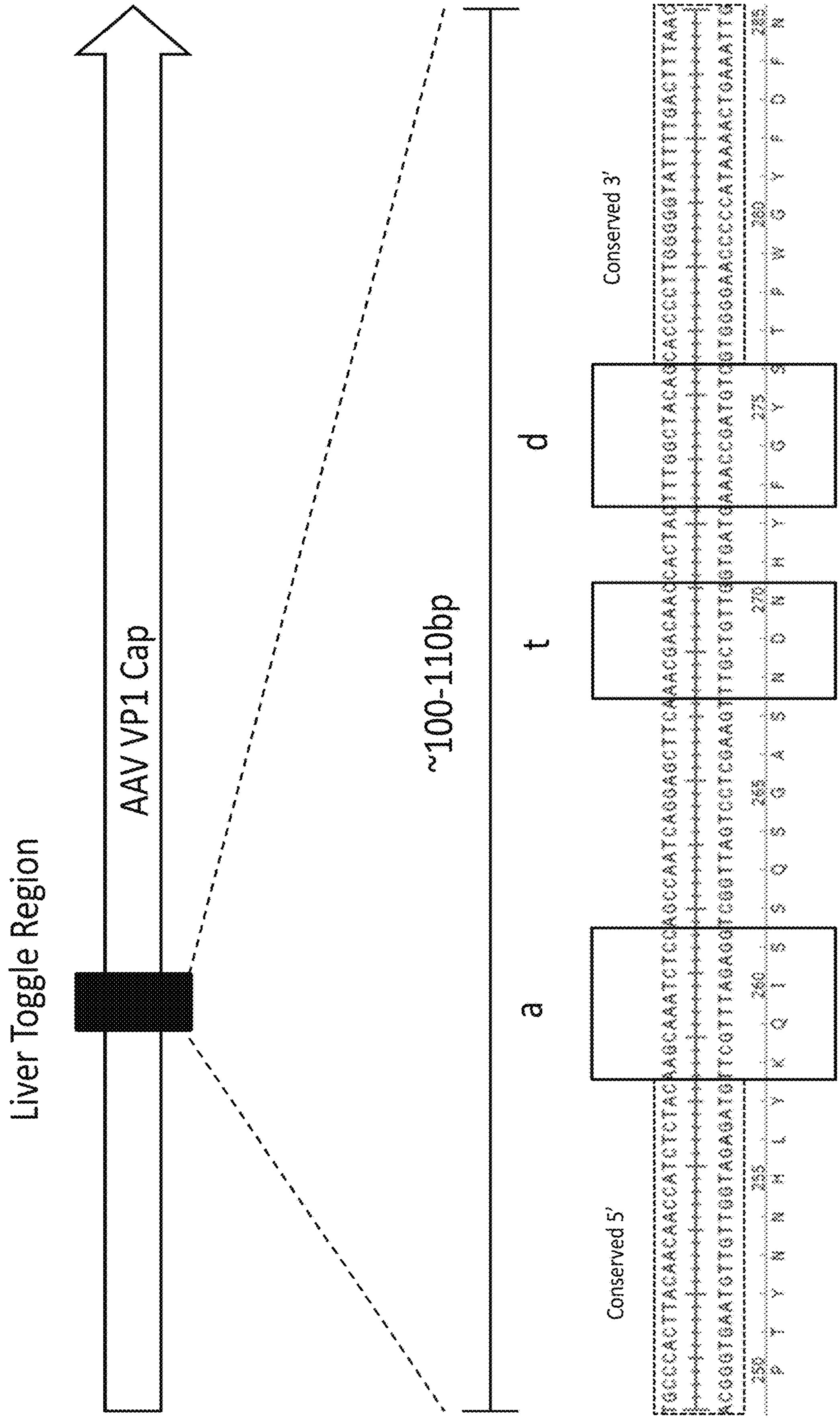
FIG. 16 is a schematic showing a method for testing the portability of the Liver Toggle Region to heterologous AAV Caps, and to further test single-residue toggle observation. Flanking the region are two conserved domains amenable to homology-directed assembly of region "swaps." SEQ ID NO:86.

Beyond the single-residue liver toggle identified herein, the liver toggle region in entirety may both import the toggle function to a heterologous serotype as well as retain other desired features of the liver toggle source serotype. FIG. 16 describes a method to test the portability of the liver toggle region rapidly and easily by taking advantage of conserved domains that flank these residues. The amplification or de novo synthesis of this ~100-110 bp region allows for homology-directed assembly into a heterologous serotype.

FIG. 17 lists the liver toggle region swaps assembled as part of this study and as illustrated in FIG. 16. The final two columns either report the in vivo liver toggle function in mice and primates as determined by this study in bold, or the predicted liver toggle function in italics.

Figure 18A:
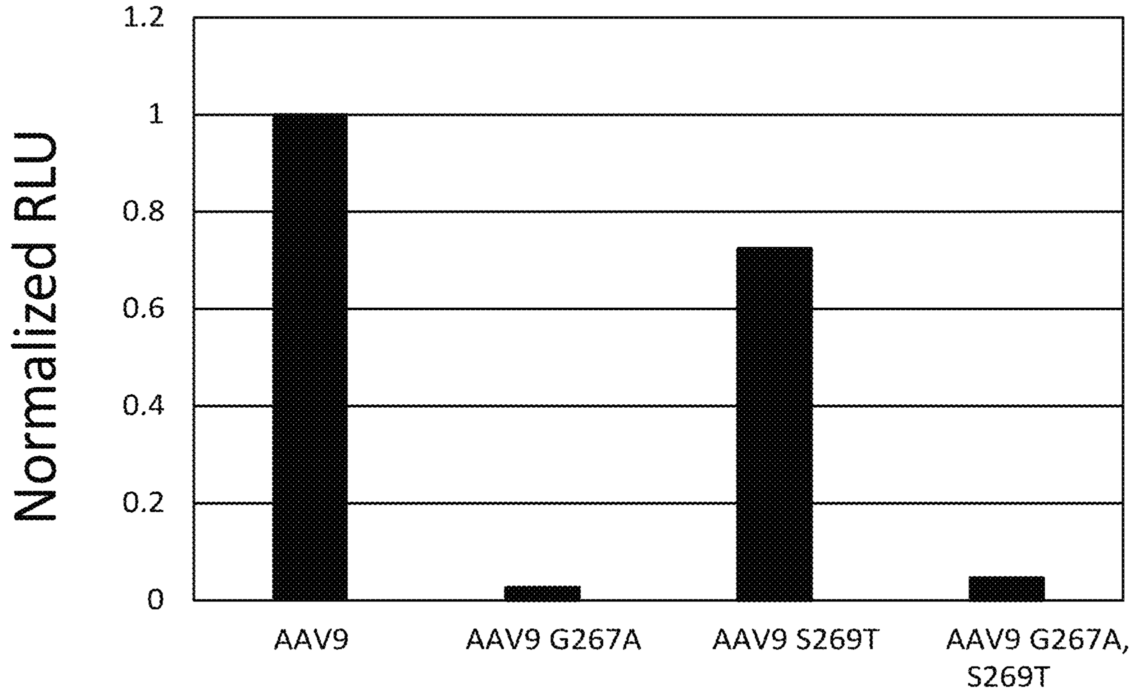
FIGS. 18A and 18B are bar graphs that report the in vitro transduction efficiencies of AAV9 and AAV9-based liver toggle variants. The variants were produced by triple transfection of 293 cells and packaged in a CMV-luciferase encoding genome. Variants were titered, and subsequently added to Huh7 cells at a multiplicity of infection (MOI) of 100,000. Huh7 cells are a hepatocarcinoma cell line, and the efficiency of transduction as reported in normalized RLUs may be interpreted as a rough indicator of whether variants were liver "on" or "off." Altering the native AAV9 G267 to A (SEQ ID NO:4) severely reduced the transduction efficiency of Huh7 cells, as did the double mutant G267A S269T (SEQ ID NO:5). AAV9 does not seem to tolerate liver toggle regions swaps well, although the toggle may be apparent in the relative efficiencies of the Anc80L65 (SEQ ID NO: 6) and Anc80L65 G266A (SEQ ID NO:7) variants.
Figure 18B:
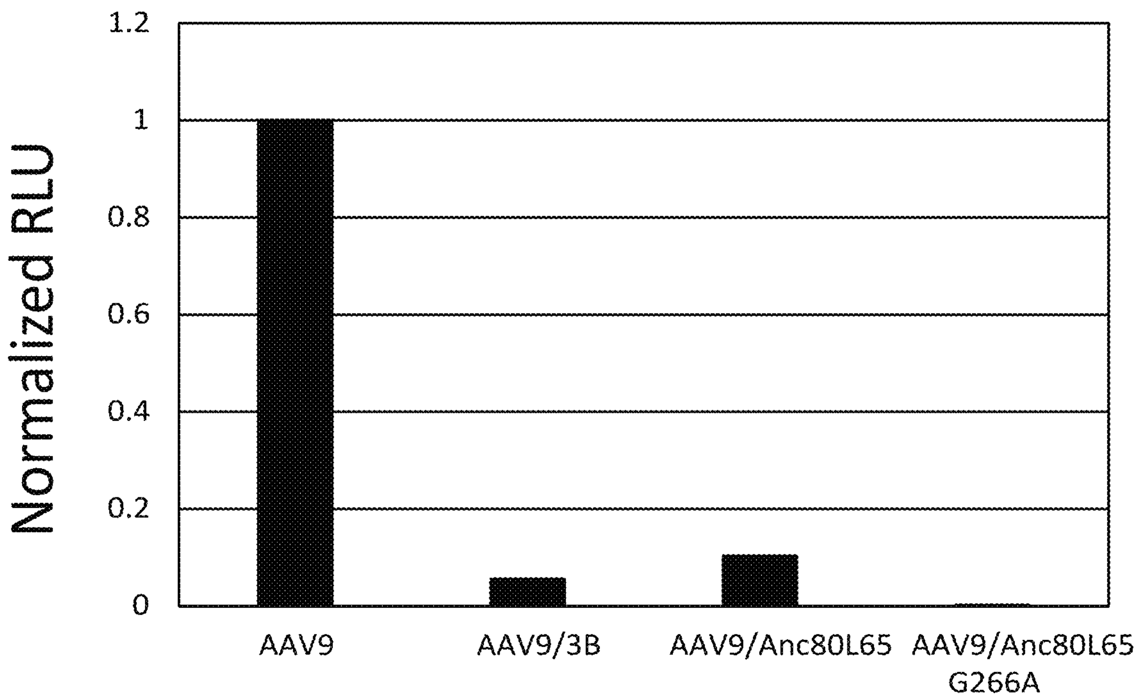

In vitro transduction of Huh7 hepatocarcinoma cells in vitro served to both test the viability of all liver toggle variants as well as suggest the liver toggle "on" or "off" phenotype of these variants in vivo. When normalized for titer, most of the engineered variants surprisingly exhibited some, if not robust, viability as determined by vector-delivered luciferase expression as reported in FIG. 18 and FIG. 19. Further, the amount of luciferase activity observed matched the predicted liver toggle phenotype, in that those variants with a liver-on "G" in the comparable position to Anc80 had higher RLU values than their liver-off "A" siblings.

Figure 20A:
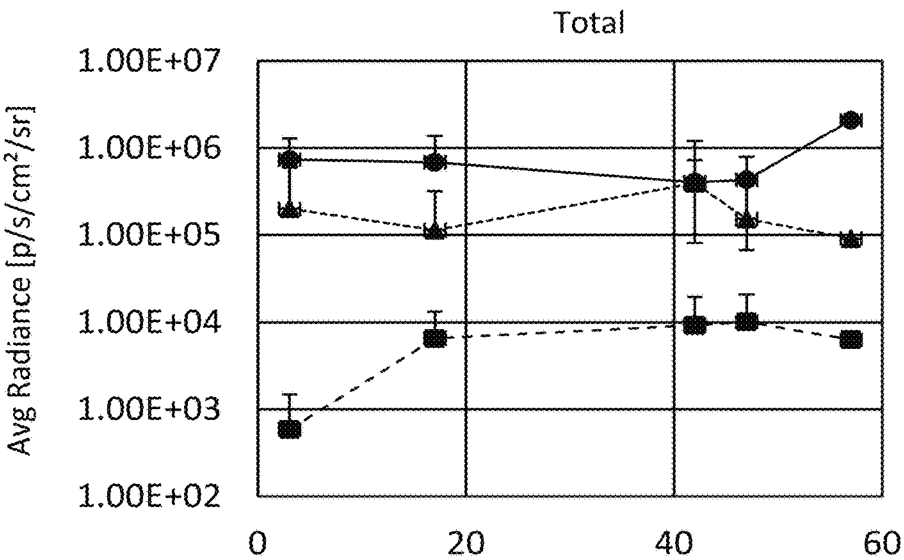
FIGS. 20A-20C are graphs showing the results of in vivo kinetic expression of luciferase from mice injected with AAV9 and the AAV9-based variants G267A and G267A S269T. Mice were followed for 57 days, with in-life imaging occurring throughout. Regions-of-interest were defined as total, liver, and haunches (the major muscle groups of the thighs and buttocks). Both liver "off" AAV9 variants have very low radiance observed within the liver region, although AAV9 G267A S269T has overall total radiance comparable to AAV9. This double mutant may produce much of this total radiance from the haunches region.
Figure 20B:
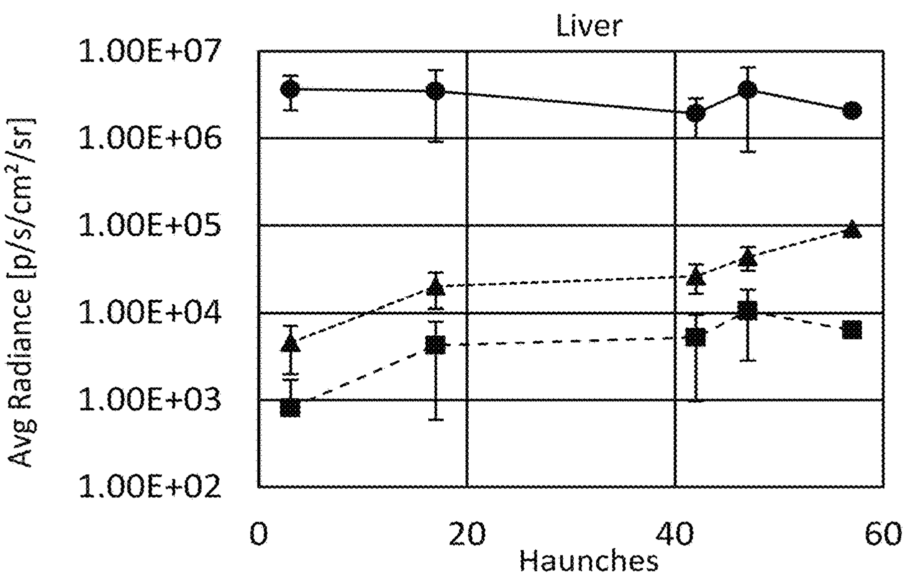
Figure 20C:
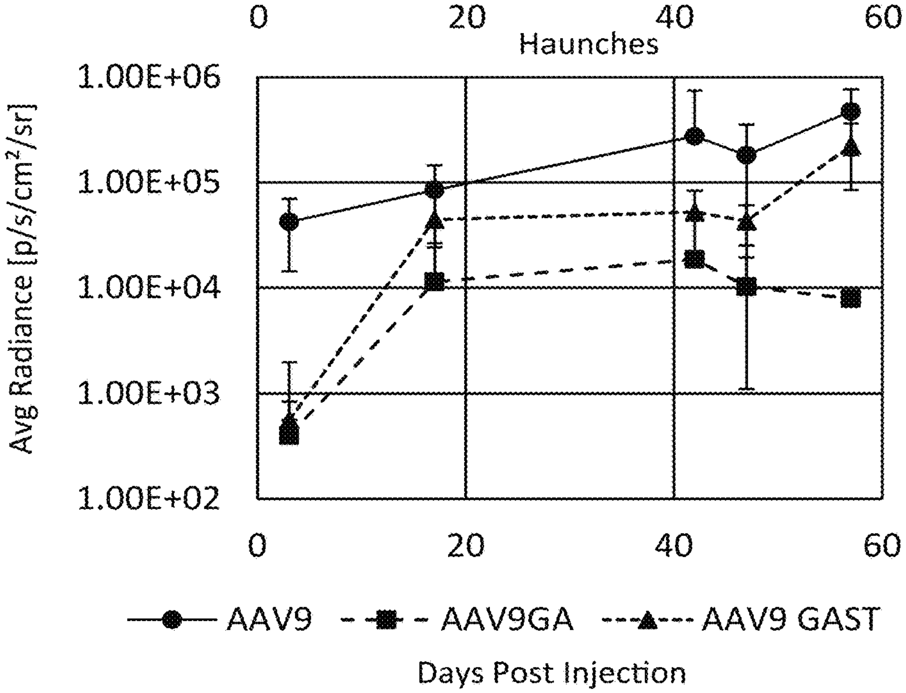
Figure 21A:
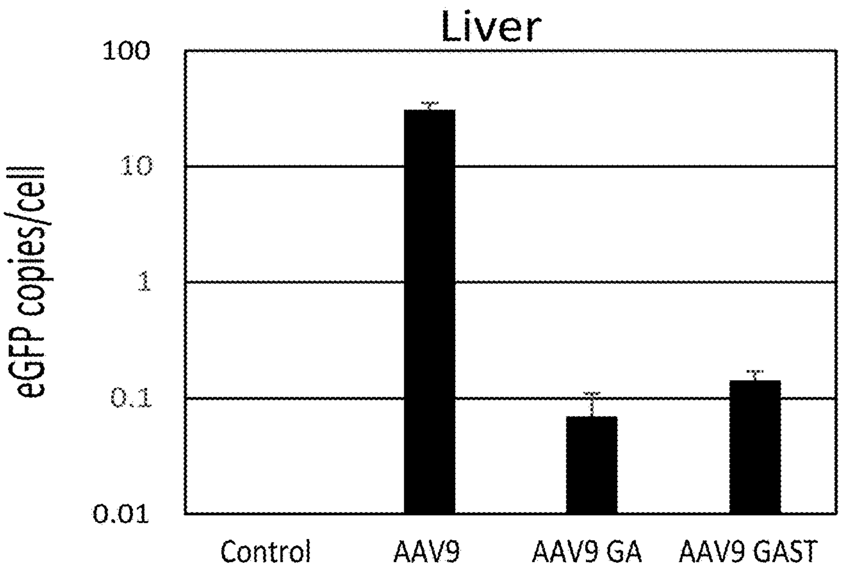
FIGS. 21A-21F are bar graphs that support the data observed from in vivo luciferase experiments. Mice injected with a GFP-expressing vectors AAV9, AAV9 G267A, or AAV9 G267A S269T, were sacrificed 28 days post-injection, and a biodistribution for both eGFP-containing genomes (DNA) and eGFP expression (RNA) was performed. Whereas both liver cell "off" mutants had three orders of magnitude lower DNA and RNA levels in the liver (FIGS. 21A-21B), in heart cells AAV9 G267A and AAV9 G267A S269T were comparable to AAV9 (FIGS. 21C-21D). Significantly, in quadriceps muscle cells, the AAV9 G267A S269T exceeded the levels of both gene delivery and gene expression of AAV9 (FIGS. 21E-21F).
Figure 21B:
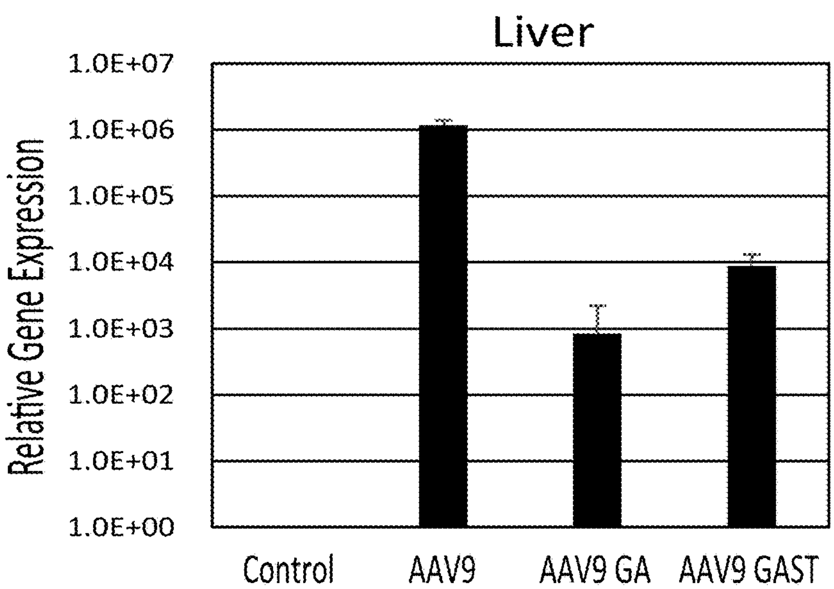
Figure 21C:
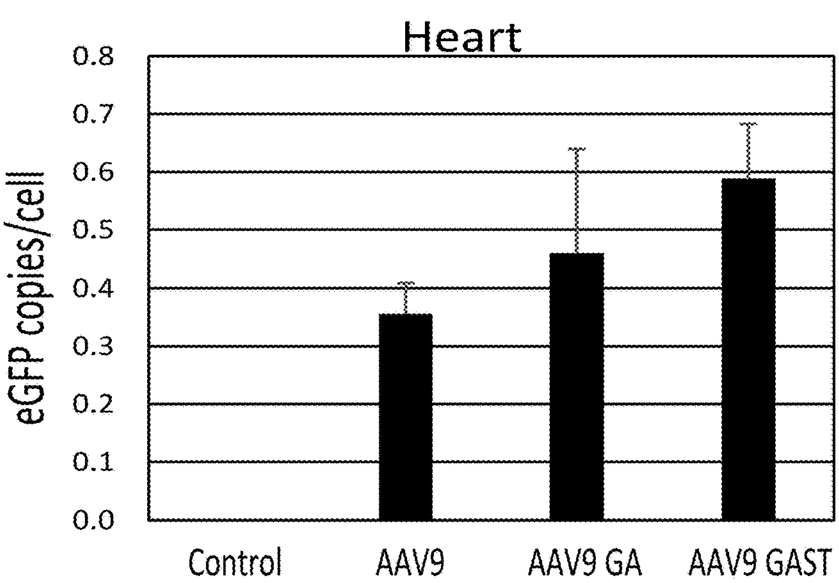
Figure 21D:
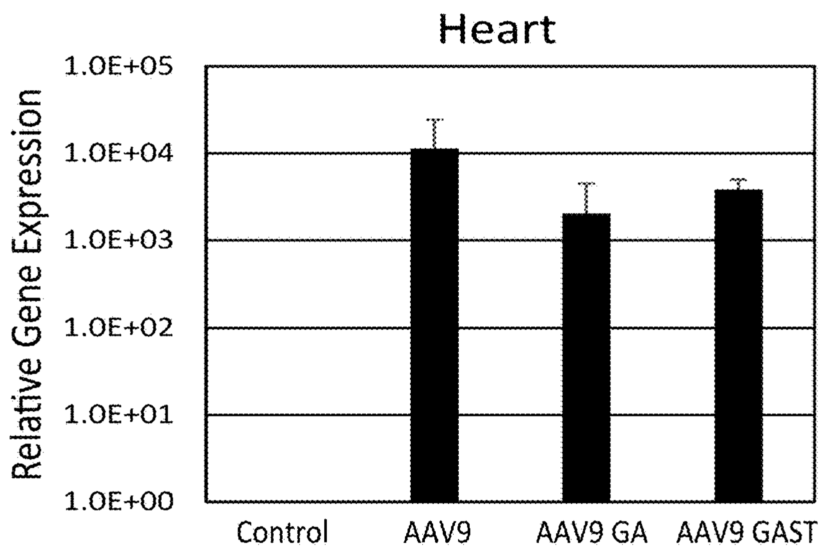
Figure 21E:
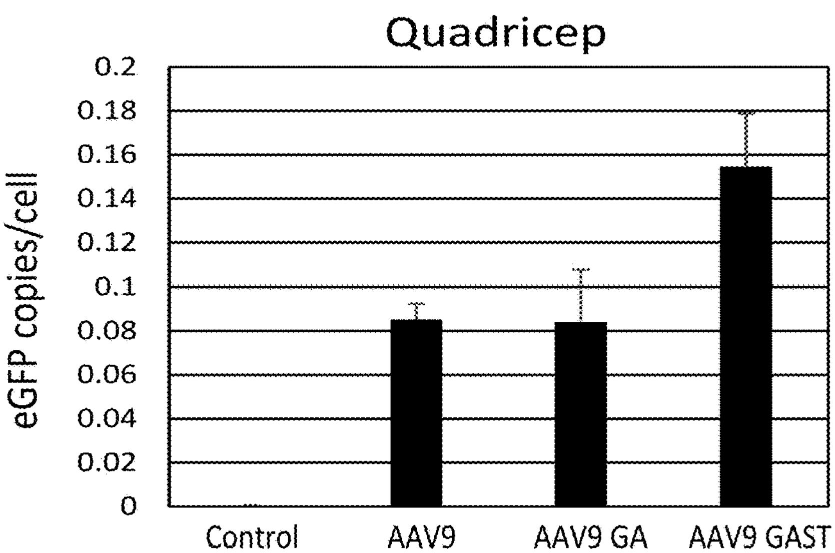
Figure 21F:
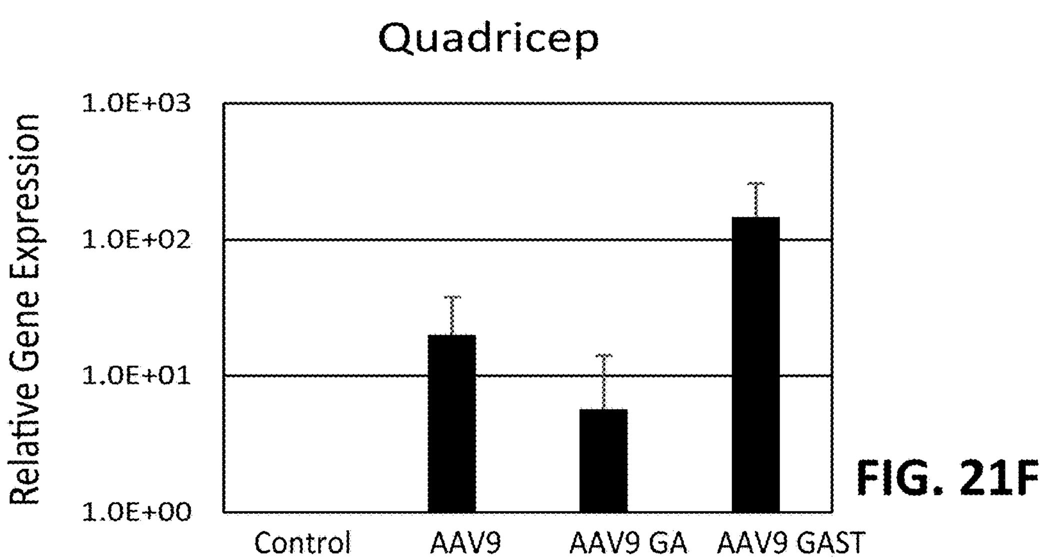

Importantly, the toggle was demonstrated in vivo at the Anc80 266-comparable position, which is position 267 in AAV9. Altering G267 to A in AAV9 reduces in-life luciferase signal, genome copies per cell and delivered marker expression by orders of magnitude in the liver as reported in FIG. 20 and FIG. 21. Further, the necessity of altering other toggle region residues is demonstrated by the superior performance of the double mutant AAV9 G267A S269T versus the toggle-alone mutant AAV9 G267A. The double mutant not only exhibits the liver "off" phenotype, but the results suggest a benefit of gene delivery to the heart and skeletal muscle.

Further work with NHPs, a human liver xenotransplantation model in FRG mice, and an in vitro human liver model, identified a second position that influences liver gene delivery by AAV, herein called "liver toggle 2." This toggle is encoded by the residue X1 in the Anc80 scaffold, which corresponds to position 168 in Anc80L65.

Figure 22A:
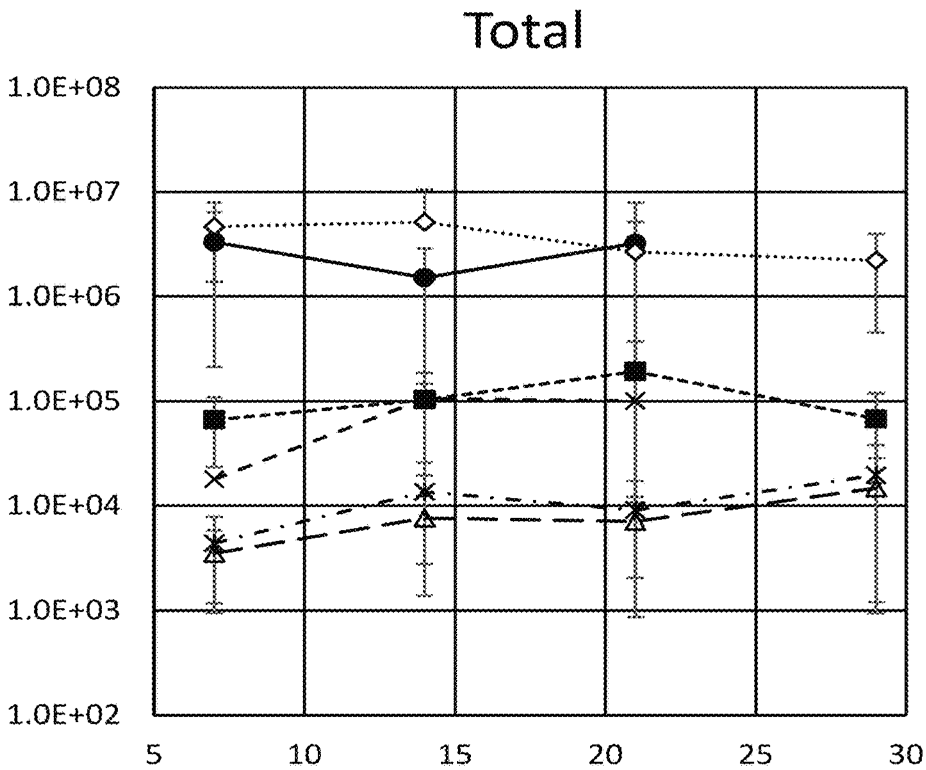
FIGS. 22A and 22B are graphs that show the results of the in vivo kinetic expression of luciferase from mice injected with AAV3B or the AAV3B-based variants G265_A266A, G265_A266G, Anc80L65-VRI, Anc80L65 G266A-VRI, or AAV9. Mice were followed for 29 days, with in-life imaging occurring throughout. Regions-of-interest were defined as total and liver. The liver "on" variants of AAV3B both emitted greater radiance than their liver "off" counterparts, supporting the toggle hypothesis. In fact, both liver "off" AAV3B variants have very low radiance observed within the liver region. Interestingly, the Anc80L65-VRI mutant performed as well as wild-type AAV3B, but, significantly, the simple insertion of a glycine created a vector that equaled AAV9 for liver region signal. The total signal, where the variant again matches AAV9, suggests that much of the AAV3B G265 A266G signal is coming from the liver.
Figure 22B:
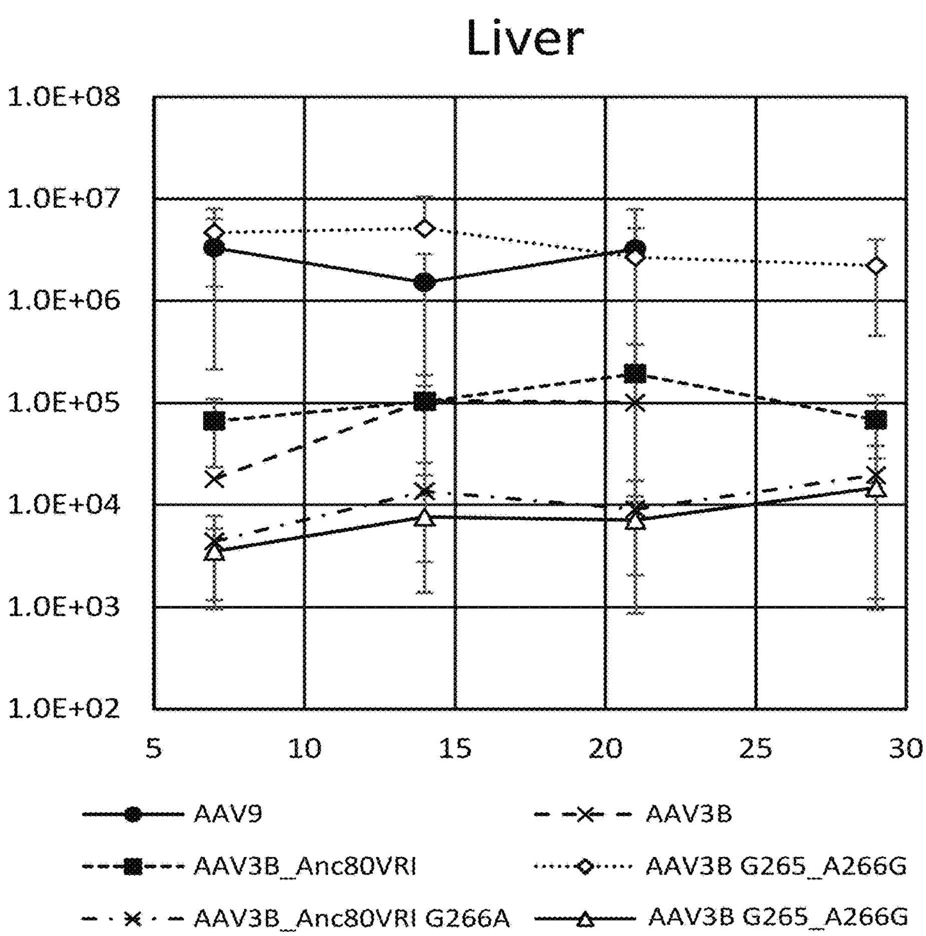

FIG. 22 demonstrates by in-life luciferase expression that a putative liver toggle "off" virus, AAV3B, can be made liver "on by either altering A266 to G and inserting a T two residues C-terminal (SEQ ID NO: 9), or inserting a G prior to A266 with or without altering the residue at position 268 from S to T (SEQ ID NO: 11). The liver "off" expectation is observed with the matched A "off" insertions of these latter two variants (SEQ ID NO: 10). Further, swapping the native AAV3B liver toggle "off" region for the liver toggle "on" regions from AAV9 (SEQ ID NO: 14) and Anc80L65 (SEQ ID NO: 15) also improve murine liver transduction. Swapping in the liver toggle "off" Anc80L65 G266A reduces in vivo luciferase expression compared to its "on" counterpart Anc80L65 (SEQ ID NO: 16).

Figure 24:
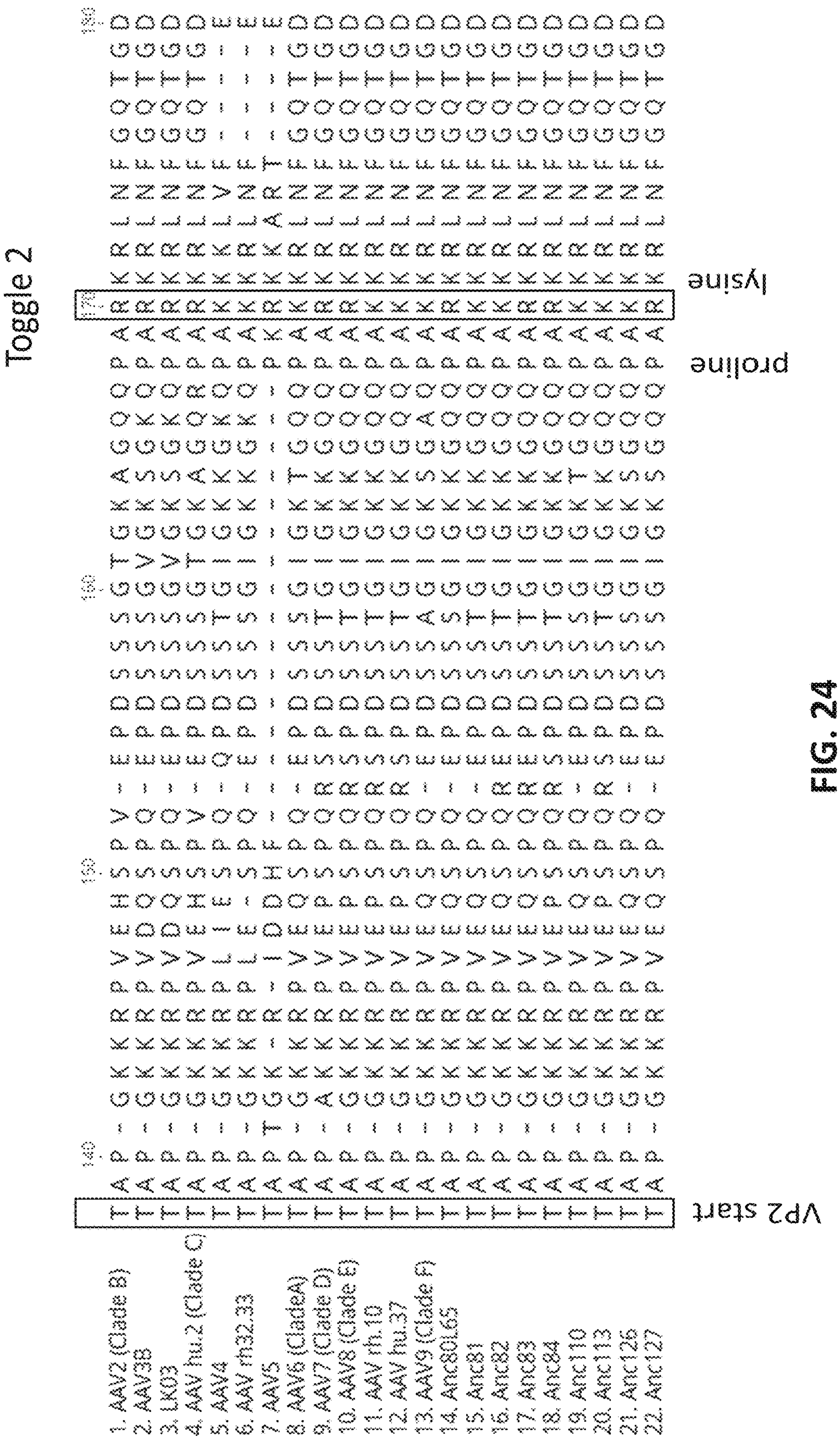
FIG. 24 is a sequence alignment of archetypes of AAV clades and clones (e.g., rows 1, 4, 8-10 and 13), clinically relevant serotypes of AAV (both naturally-occurring and engineered; e.g., rows 2, 3, 5-7, 11, and 12), and Anc variants (e.g., rows 14-22). Rows 1-22 correspond to SEQ ID NOs: 64-85. The location of Liver Toggle 2, the orienting conserved proline and lysine, and the non-canonical start codon of VP2, are indicated. Liver Toggle 2 represents residue 168 in Anc80L65 and AAV9, and 151 in AAV5, emphasizing that position number is relative when defining the toggle.

FIG. 24 identifies the location and local context of X1 in clinically relevant serotypes and AncAAVs. It is located in a positively-charged motif close to the N-terminus of VP2, readily identifiable by sequence alignment in all AAVs except AAV5, whose VP2 N-terminus is 17-20 residues shorter. Nonetheless, all serotypes can define liver toggle 2 by its relationship to conserved flanking residues: a proline two residues N-terminal and a lysine one residue C-terminal.

Figure 25A:
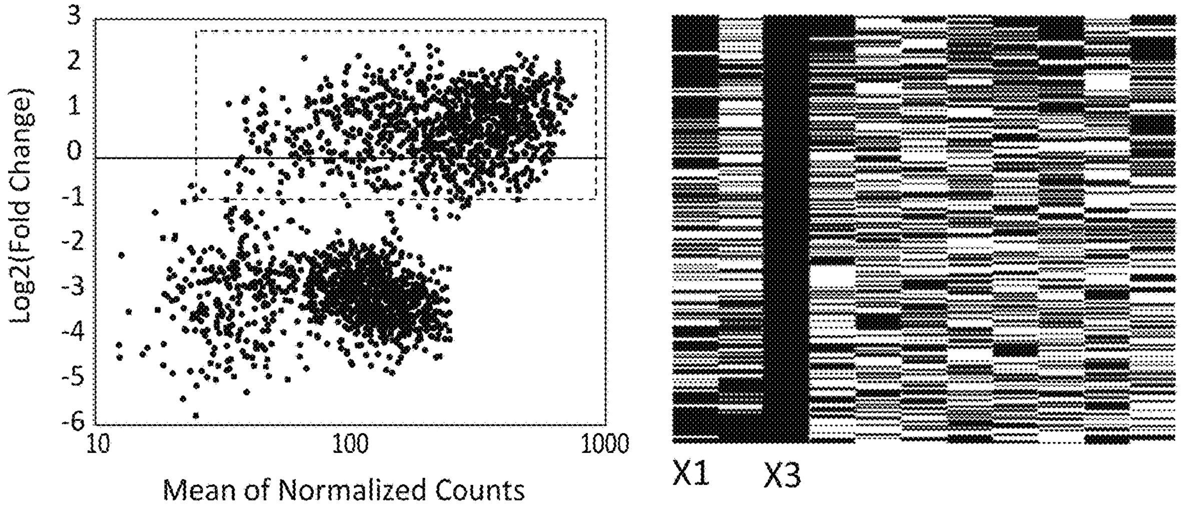
FIGS. 25A and 25B represent graphs and heat maps.
Figure 25B:
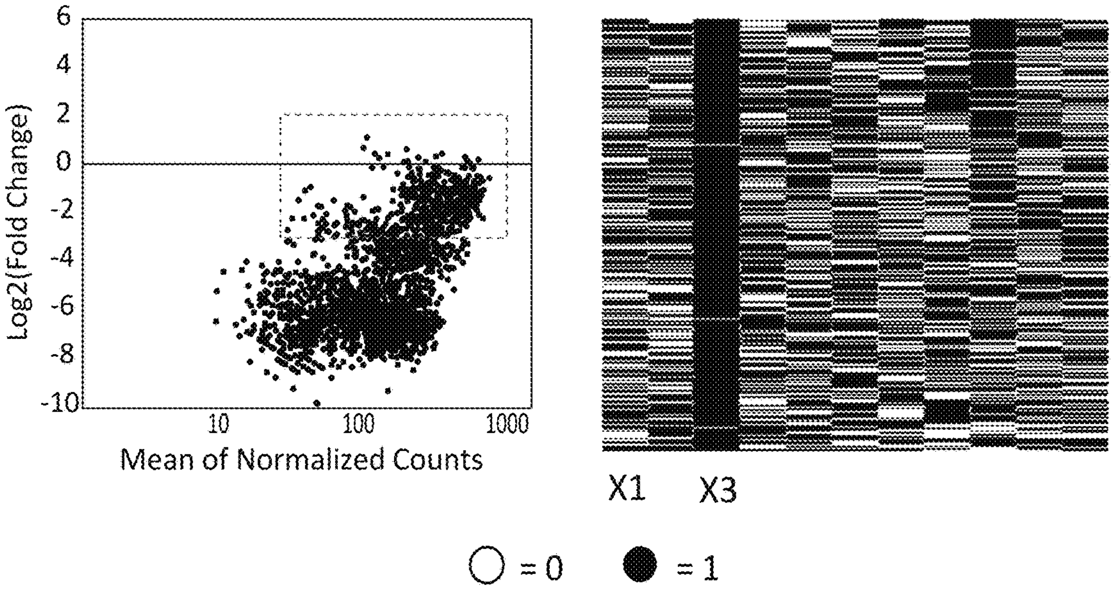
Figure 26A:
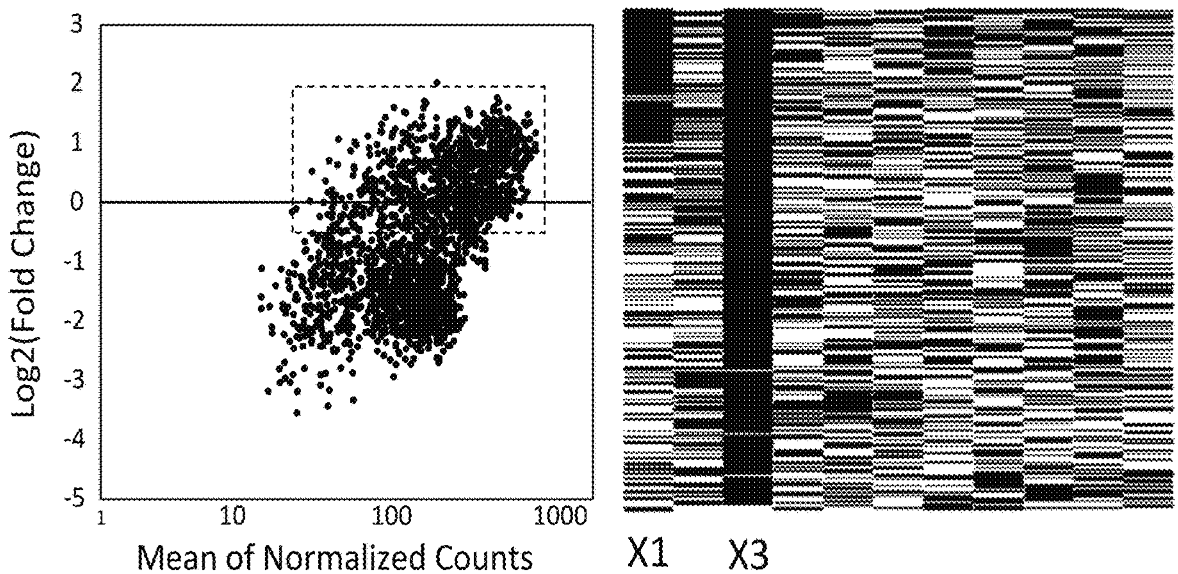
FIGS. 26A-26C are three MA plots on the left showing the abundance of the 2048 Anc80 library members in NHP (FIG. 26A) at day 28, xenografted FRG mouse model (FIG. 26B) at day 28, and human hepatocytes (FIG. 26C) at day 3, in animal and in vitro models, versus viral input. The variants that are enriched in these cells have been boxed, and identity of each of 11 toggle positions is indicated in the "heatmap" on the right in each figure. Of eleven toggled positions, the liver toggle position X3 correlates with enrichment. Position X1 Toggle 2, state 1, also correlates with enrichment, markedly so with the most enriched variants.
Figure 26B:
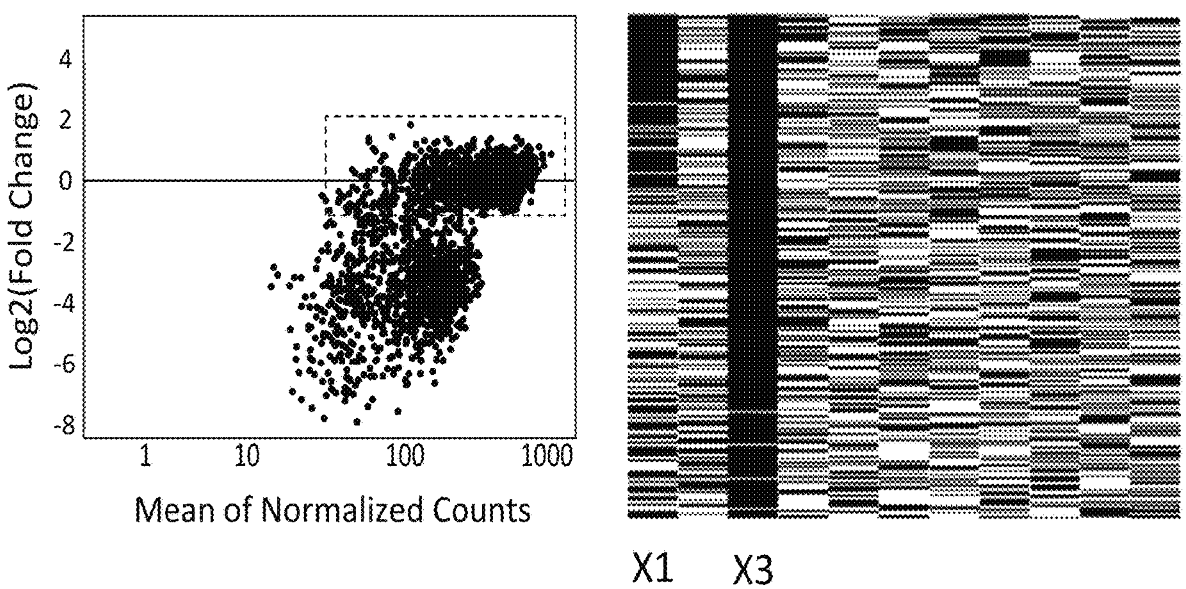
Figure 26C:
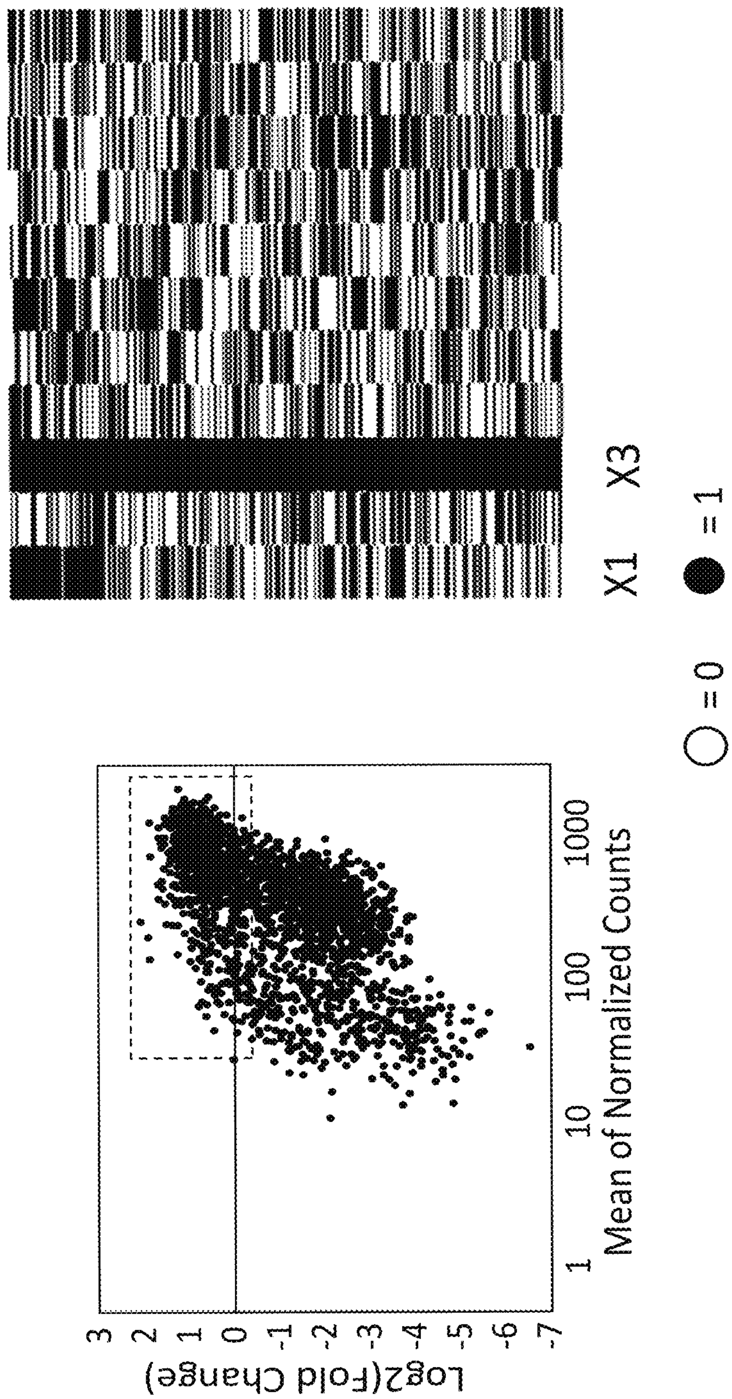

FIG. 25 and FIG. 26 illustrate the relevance of liver toggle 2 to liver enrichment. In FIG. 25, the experiments queried the enrichment of Anc80 variants in both wild-type C57BL/6 mice and the murine hepatocyte component of the human liver xenograft mouse model FRG. In FIG. 26, the experiments queried the enrichment of Anc80 variants in rhesus macaque livers, the reciprocal human hepatocytes from the FRG experiment, and in human hepatocytes cultured in vitro using a technique called micro patterned co-culture (MPCC). In each case, when liver-enriched variants were selected from the accompanying MA plots, the relevance of the liver toggle X3 was clear. Additionally, the relevance of position X1 was apparent, with variants switching from toggle 0=K to toggle 1=R as the enrichment rises in rank order from bottom to top. This pattern suggests that liver toggle 2 at position X1 is independent of the liver toggle at position X3, but that the toggle at X3 is the dominant position.

AAV3B has gained popularity as a clinically relevant serotype since the discovery that it relies upon human hepatocyte growth factor receptor (HuHGFR) for efficient hepatocyte entry (Ling et al., 2010, Hum. Gen. Ther, 21 (12): 1741-1747). Prior to this discovery, this serotype was dismissed by gene therapists due to its poor liver-delivery performance in mice. Nonetheless, most preclinical disease models are in mice, and these mouse models serve an essential role in, for example, determining efficacy, safety, and dose determination of gene therapy therapeutics. Engineering AAV3B so that it retains its desirable therapeutic characteristics while improving its liver-delivery performance in mice to equivalent levels as primates would be extremely valuable to the industry. AAV3B has a foreshortened VRI and liver toggle region compared to Anc80, making it difficult to assign a residue as being Anc80 position 266 comparable (see FIG. 14 and FIG. 15).

Figure 19A:
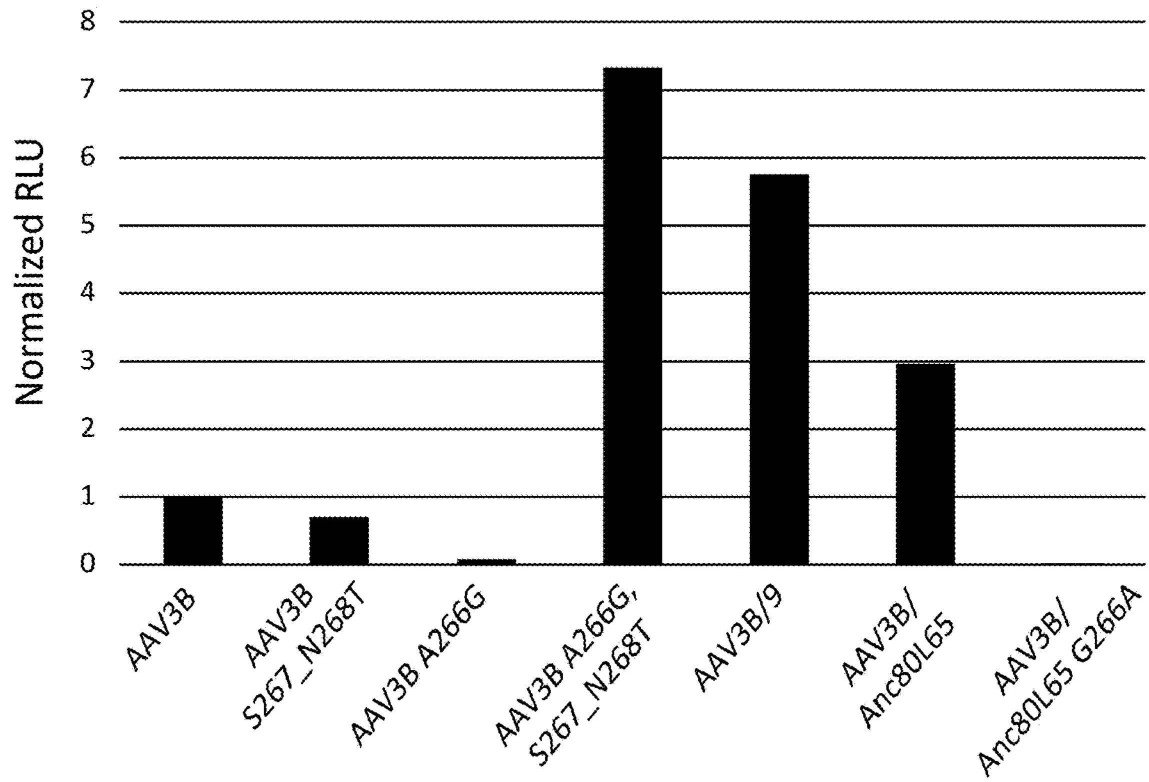
FIGS. 19A and 19B are bar graphs that report the in vitro transduction efficiencies of AAV3B and AAV3B-based liver toggle variants. The variants were produced by triple transfection of 293 cells and packaged in a CMV-luciferase encoding genome. Variants were titered, and subsequently added to Huh7 cells at an MOI of 100,000. Huh7 cells are a hepatocarcinoma cell line, and the efficiency of transduction as reported in normalized RLUs may be interpreted as a rough indicator of whether variants were liver "on" or "off." Altering the native AAV3B A266 to G (SEQ ID NO:8) unexpectedly severely reduced the transduction efficiency of Huh7 cells, but insertion of a T at the corresponding location in Anc80L65 (SEQ ID NO:9) rescued this variant and outperformed AAV3B. Similarly the insertion of an A (SEQ ID NO: 10) or a G (SEQ ID NO: 11) before A266, with or without the alteration S268T (SEQ ID NO:12 and SEQ ID NO: 13), results in a liver toggle-like efficiency pattern with both +G "on" variants outperforming AAV3B. AAV3B tolerates liver toggle regions swaps well, with the toggle apparent in the liver "on" AAV9 variant (SEQ ID NO: 14), and the relative efficiencies of the Anc80L65 (SEQ ID NO:15) and Anc80L65 G266A (SEQ ID NO:16) variants.
Figure 19B:
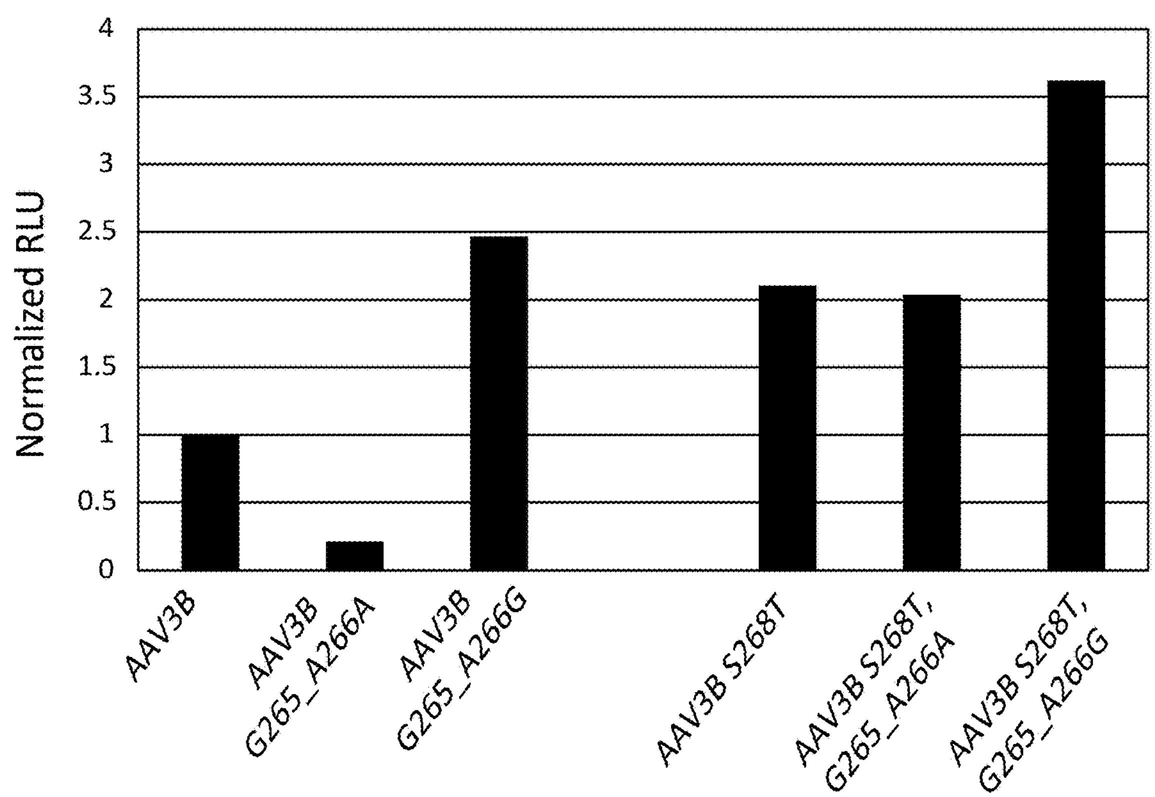

Altering the A at position 266 to a G does not improve gene delivery to Huh7 cells; in fact, this alteration may produce a loss-of-function phenotype to AAV3B. Reinforcing the necessity of considering the entire liver toggle region in engineering desirable characteristics, either inserting a T at the comparable position to Anc80 in AAV3B in conjunction with altering A266 to G, or inserting either an A or a G at what would be the comparable in Anc80, creates variants that both exhibit liver "on" and "off" phenotypes in Huh7 cells and in vivo (FIG. 19 and FIG. 22). Further, AAV3B seems to tolerate liver toggle region swaps well, and importing liver "on" liver toggle regions from AAV9 and Anc80L65 improves the Huh7 and in vivo murine hepatocyte gene delivery of these variants versus AAV3B alone. Importing the liver "off" Anc80L65 G266A liver toggle region reduces this ability to near background levels (FIG. 19 and FIG. 22). Importantly, the single insertion of a G between G265 and A266 creates a 3B-based serotype that performs equally as well as AAV9 in mice as determined by luciferase signal in the liver (FIG. 22).

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An adeno-associated virus (AAV) comprising a capsid protein, which comprises the amino acid sequence as set forth in:

a) SEQ ID NO:87, which corresponds to an AAV9 capsid protein comprising a modification in its liver toggle site to comprise AAV3B-VR1 (SQSGASNDN, SEQ ID NO: 58);

b) SEQ ID NO:88, which corresponds to an AAV80L65 capsid protein comprising a modification in its liver toggle site to comprise AAV3B-VR1 (SQSGASNDN, SEQ ID NO: 58);

c) SEQ ID NO:89, which corresponds to an AAV80L65 capsid protein comprising a modification in its liver toggle site to comprise AAV9-VR1 (NSTSGGSSNDN; SEQ ID NO: 62); or d) SEQ ID NO:90, which corresponds to an AAV3B capsid protein comprising an S268T modification.

2. The adeno-associated virus (AAV) of claim 1, wherein the capsid protein comprises the amino acid sequence as set forth in SEQ ID NO:87, which corresponds to an AAV9 capsid protein comprising a modification in its liver toggle site to comprise AAV3B-VR1 (SQSGASNDN, SEQ ID NO: 58).

3. The adeno-associated virus (AAV) of claim 1, wherein the capsid protein comprises the amino acid sequence as set forth in SEQ ID NO:88, which corresponds to an AAV80L65 capsid protein comprising a modification in its liver toggle site to comprise AAV3B-VR1 (SQSGASNDN, SEQ ID NO: 63).

4. The adeno-associated virus (AAV) of claim 1, wherein the capsid protein comprises the amino acid sequence as set forth in SEQ ID NO:89, which corresponds to an AAV80L65 capsid protein comprising a modification in its liver toggle site to comprise AAV9-VR1 (NSTSGGSSNDN; SEQ ID NO: 62).

5. The adeno-associated virus (AAV) of claim 1, wherein the capsid protein comprises the amino acid sequence as set forth in SEQ ID NO:90, which corresponds to an AAV3B capsid protein comprising an S268T modification.

6. A method of altering tissue tropism of an adeno-associated virus (AAV) comprising:

a) modifying the liver toggle site in an AAV9 capsid protein to comprise AAV3B-VR1 (SQSGASNDN, SEQ ID NO: 58), which results in a capsid protein having the amino acid sequence as set forth in SEQ ID NO:87;

b) modifying the liver toggle site in an AAV80L65 capsid protein to comprise AAV3B-VR1 (SQSGASNDN, SEQ ID NO: 58), which results in a capsid protein having the amino acid sequence as set forth in SEQ ID NO:88;

c) modifying the liver toggle site in an AAV80L65 capsid protein to comprise AAV9-VR1 (NSTSGGSSNDN; SEQ ID NO: 62), which results in a capsid protein having the amino acid sequence as set forth in SEQ ID NO:89; or d) modifying the liver toggle site in an AAV3B capsid protein to comprise an S268T modification, which results in a capsid protein having the amino acid sequence as set forth in SEQ ID NO:90.

* * * * *

SEQUENCE LISTING

```
Sequence total quantity: 90
SEQ ID NO: 1            moltype = AA  length = 736
FEATURE                 Location/Qualifiers
REGION                  1..736
                        note = MISC_FEATURE - /note="Variant residues given in the
                         sequence have no preference with respect to those in the
                         annotations for variant positions"
VARIANT                 168
                        note = /replace="Arg"
VARIANT                 204
                        note = /replace="Ser"
VARIANT                 266
                        note = /replace="Gly"
VARIANT                 311
                        note = /replace="Lys"
VARIANT                 411
                        note = /replace="Gln"
VARIANT                 460
                        note = /replace="Glu"
VARIANT                 493
                        note = /replace="Thr"
VARIANT                 562
                        note = /replace="Asn"
VARIANT                 576
                        note = /replace="Glu"
VARIANT                 587
                        note = /replace="Ala"
VARIANT                 609
                        note = /replace="Asp"
source                  1..736
                        mol_type = protein
                        organism = Adeno-associated virus
SEQUENCE: 1
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPAXKR LNFGQTGDSE  180
SVPDPQPLGE PPAAPSGVGS NTMXAGGGAP MADNNEGADG VGNASGNWHC DSTWLGDRVI  240
TTSTRTWALP TYNNHLYKQI SSQSGXSTND NTYFGYSTPW GYFDFNRFHC HFSPRDWQRL  300
INNNWGFRPK XLNFKLFNIQ VKEVTTNDGT TTIANNLTST VQVFTDSEYQ LPYVLGSAHQ  360
GCLPPFPADV FMIPQYGYLT LNNGSQAVGR SSFYCLEYFP SQMLRTGNNF XFSYTFEDVP  420
FHSSYAHSQS LDRLMNPLID QYLYYLSRTQ TTSGTAGNRX LQFSQAGPSS MANQAKNWLP  480
GPCYRQQRVS KTXNQNNNSN FAWTGATKYH LNGRDSLVNP GPAMATHKDD EDKFFPMSGV  540
LIFGKQGAGN SNVDLDNVMI TXEEEIKTTN PVATEXYGTV ATNLQSXNTA PATGTVNSQG  600
ALPGMVWQXR DVYLQGPIWA KIPHTDGHFH PSPLMGGFGL KHPPPQILIK NTPVPANPPT  660
TFSPAKFASF ITQYSTGQVS VEIEWELQKE NSKRWNPEIQ YTSNYNKSTN VDFAVDTNGV  720
YSEPRPIGTR YLTRNL                                                 736

SEQ ID NO: 2            moltype = AA  length = 736
FEATURE                 Location/Qualifiers
source                  1..736
```

```
                         mol_type = protein
                         organism = Adeno-associated virus
SEQUENCE: 2
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPARKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI SSQSGGSTND NTYFGYSTPW GYFDFNRFHC HFSPRDWQRL  300
INNNWGFRPK KLNFKLFNIQ VKEVTTNDGT TTIANNLTST VQVFTDSEYQ LPYVLGSAHQ  360
GCLPPFPADV FMIPQYGYLT LNNGSQAVGR SSFYCLEYFP SQMLRTGNNF QFSYTFEDVP  420
FHSSYAHSQS LDRLMNPLID QYLYYLSRTQ TTSGTAGNRT LQFSQAGPSS MANQAKNWLP  480
GPCYRQQRVS KTTNQNNNSN FAWTGATKYH LNGRDSLVNP GPAMATHKDD EDKFFPMSGV  540
LIFGKQGAGN SNVDLDNVMI TNEEEIKTTN PVATEEYGTV ATNLQSANTA PATGTVNSQG  600
ALPGMVWQDR DVYLQGPIWA KIPHTDGHFH PSPLMGGFGL KHPPPQILIK NTPVPANPPT  660
TFSPAKFASF ITQYSTGQVS VEIEWELQKE NSKRWNPEIQ YTSNYNKSTN VDFAVDTNGV  720
YSEPRPIGTR YLTRNL                                                  736

SEQ ID NO: 3             moltype = AA  length = 736
FEATURE                  Location/Qualifiers
source                   1..736
                         mol_type = protein
                         organism = Adeno-associated virus
SEQUENCE: 3
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPARKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI SSQSGASTND NTYFGYSTPW GYFDFNRFHC HFSPRDWQRL  300
INNNWGFRPK KLNFKLFNIQ VKEVTTNDGT TTIANNLTST VQVFTDSEYQ LPYVLGSAHQ  360
GCLPPFPADV FMIPQYGYLT LNNGSQAVGR SSFYCLEYFP SQMLRTGNNF QFSYTFEDVP  420
FHSSYAHSQS LDRLMNPLID QYLYYLSRTQ TTSGTAGNRT LQFSQAGPSS MANQAKNWLP  480
GPCYRQQRVS KTTNQNNNSN FAWTGATKYH LNGRDSLVNP GPAMATHKDD EDKFFPMSGV  540
LIFGKQGAGN SNVDLDNVMI TNEEEIKTTN PVATEEYGTV ATNLQSANTA PATGTVNSQG  600
ALPGMVWQDR DVYLQGPIWA KIPHTDGHFH PSPLMGGFGL KHPPPQILIK NTPVPANPPT  660
TFSPAKFASF ITQYSTGQVS VEIEWELQKE NSKRWNPEIQ YTSNYNKSTN VDFAVDTNGV  720
YSEPRPIGTR YLTRNL                                                  736

SEQ ID NO: 4             moltype = AA  length = 736
FEATURE                  Location/Qualifiers
source                   1..736
                         mol_type = protein
                         organism = Adeno-associated virus
SEQUENCE: 4
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGASSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 5             moltype = AA  length = 736
FEATURE                  Location/Qualifiers
source                   1..736
                         mol_type = protein
                         organism = Adeno-associated virus
SEQUENCE: 5
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGASTN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 6             moltype = AA  length = 735
FEATURE                  Location/Qualifiers
```

-continued

```
source                  1..735
                        mol_type = protein
                        organism = Adeno-associated virus
SEQUENCE: 6
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SSQSGGSTND NTYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELQKEN SKRWNPEIQY TSNYYKSNNV EFAVNTEGVY  720
SEPRPIGTRY LTRNL                                                  735

SEQ ID NO: 7            moltype = AA  length = 735
FEATURE                 Location/Qualifiers
source                  1..735
                        mol_type = protein
                        organism = Adeno-associated virus
SEQUENCE: 7
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SSQSGASTND NTYFGYSTPW GYFDFNRFHC HFSPRDWQRL  300
INNNWGFRPK RLNFKLFNIQ VKEVTDNNGV KTIANNLTST VQVFTDSDYQ LPYVLGSAHE  360
GCLPPFPADV FMIPQYGYLT LNDGSQAVGR SSFYCLEYFP SQMLRTGNNF QFSYEFENVP  420
FHSSYAHSQS LDRLMNPLID QYLYYLSKTI NGSGQNQQTL KFSVAGPSNM AVQGRNYIPG  480
PSYRQQRVST TVTQNNNSEF AWPGASSWAL NGRNSLMNPG PAMASHKEGE DRFFPLSGSL  540
IFGKQGTGRD NVDADKVMIT NEEEIKTTNP VATESYGQVA TNHQSAQAQA QTGWVQNQGI  600
LPGMVWQDRD VYLQGPIWAK IPHTDGNFHP SPLMGGFGMK HPPPQILIKN TPVPADPPTA  660
FNKDKLNSFI TQYSTGQVSV EIEWELQKEN SKRWNPEIQY TSNYYKSNNV EFAVNTEGVY  720
SEPRPIGTRY LTRNL                                                  735

SEQ ID NO: 8            moltype = AA  length = 736
FEATURE                 Location/Qualifiers
source                  1..736
                        mol_type = protein
                        organism = Adeno-associated virus
SEQUENCE: 8
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGGSNDN HYFGYSTPWG YFDFNRFHCH FSPRDWQRLI  300
NNNWGFRPKK LSFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSLQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTRTVNDQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRNL                                                 736

SEQ ID NO: 9            moltype = AA  length = 737
FEATURE                 Location/Qualifiers
source                  1..737
                        mol_type = protein
                        organism = Adeno-associated virus
SEQUENCE: 9
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGGSTND NHYFGYSTPW GYFDFNRFHC HFSPRDWQRL  300
INNNWGFRPK KLSFKLFNIQ VKEVTQNDGT TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRNL                                                737

SEQ ID NO: 10           moltype = AA  length = 737
```

-continued

```
FEATURE                Location/Qualifiers
source                 1..737
                       mol_type = protein
                       organism = Adeno-associated virus
SEQUENCE: 10
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGAASND NHYFGYSTPW GYFDFNRFHC HFSPRDWQRL  300
INNNWGFRPK KLSFKLFNIQ VKEVTQNDGT TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRNL                                                 737

SEQ ID NO: 11          moltype = AA  length = 737
FEATURE                Location/Qualifiers
source                 1..737
                       mol_type = protein
                       organism = Adeno-associated virus
SEQUENCE: 11
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGGASND NHYFGYSTPW GYFDFNRFHC HFSPRDWQRL  300
INNNWGFRPK KLSFKLFNIQ VKEVTQNDGT TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRNL                                                 737

SEQ ID NO: 12          moltype = AA  length = 737
FEATURE                Location/Qualifiers
source                 1..737
                       mol_type = protein
                       organism = Adeno-associated virus
SEQUENCE: 12
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGAATND NHYFGYSTPW GYFDFNRFHC HFSPRDWQRL  300
INNNWGFRPK KLSFKLFNIQ VKEVTQNDGT TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRNL                                                 737

SEQ ID NO: 13          moltype = AA  length = 737
FEATURE                Location/Qualifiers
source                 1..737
                       mol_type = protein
                       organism = Adeno-associated virus
SEQUENCE: 13
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGGATND NHYFGYSTPW GYFDFNRFHC HFSPRDWQRL  300
INNNWGFRPK KLSFKLFNIQ VKEVTQNDGT TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRNL                                                 737
```

-continued

```
SEQ ID NO: 14          moltype = AA  length = 738
FEATURE                Location/Qualifiers
source                 1..738
                       mol_type = protein
                       organism = Adeno-associated virus
SEQUENCE: 14
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KKLSFKLFNI QVKEVTQNDG TTTIANNLTS TVQVFTDSEY QLPYVLGSAH  360
QGCLPPFPAD VFMVPQYGYL TLNNGSQAVG RSSFYCLEYF PSQMLRTGNN FQFSYTFEDV  420
PFHSSYAHSQ SLDRLMNPLI DQYLYYLNRT QGTTSGTTNQ SRLLFSQAGP QSMSLQARNW  480
LPGPCYRQQR LSKTANDNNN SNFPWTAASK YHLNGRDSLV NPGPAMASHK DDEEKFFPMH  540
GNLIFGKEGT TASNAELDNV MITDEEEIRT TNPVATEQYG TVANNLQSSN TAPTTRTVND  600
QGALPGMVWQ DRDVYLQGPI WAKIPHTDGH FHPSPLMGGF GLKHPPPQIM IKNTPVPANP  660
PTTFSPAKFA SFITQYSTGQ VSVEIEWELQ KENSKRWNPE IQYTSNYNKS VNVDFTVDTN  720
GVYSEPRPIG TRYLTRNL                                                738

SEQ ID NO: 15          moltype = AA  length = 737
FEATURE                Location/Qualifiers
source                 1..737
                       mol_type = protein
                       organism = Adeno-associated virus
SEQUENCE: 15
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGGSTND NTYFGYSTPW GYFDFNRFHC HFSPRDWQRL  300
INNNWGFRPK KLSFKLFNIQ VKEVTQNDGT TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GALPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRNL                                                 737

SEQ ID NO: 16          moltype = AA  length = 737
FEATURE                Location/Qualifiers
source                 1..737
                       mol_type = protein
                       organism = Adeno-associated virus
SEQUENCE: 16
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASTND NTYFGYSTPW GYFDFNRFHC HFSPRDWQRL  300
INNNWGFRPK KLSFKLFNIQ VKEVTQNDGT TTIANNLTST VQVFTDSEYQ LPYVLGSAHQ  360
GCLPPFPADV FMVPQYGYLT LNNGSQAVGR SSFYCLEYFP SQMLRTGNNF QFSYTFEDVP  420
FHSSYAHSQS LDRLMNPLID QYLYYLNRTQ GTTSGTTNQS RLLFSQAGPQ SMSLQARNWL  480
PGPCYRQQRL SKTANDNNNS NFPWTAASKY HLNGRDSLVN PGPAMASHKD DEEKFFPMHG  540
NLIFGKEGTT ASNAELDNVM ITDEEEIRTT NPVATEQYGT VANNLQSSNT APTTRTVNDQ  600
GSLPGMVWQD RDVYLQGPIW AKIPHTDGHF HPSPLMGGFG LKHPPPQIMI KNTPVPANPP  660
TTFSPAKFAS FITQYSTGQV SVEIEWELQK ENSKRWNPEI QYTSNYNKSV NVDFTVDTNG  720
VYSEPRPIGT RYLTRNL                                                 737

SEQ ID NO: 17          moltype = AA  length = 736
FEATURE                Location/Qualifiers
source                 1..736
                       mol_type = protein
                       organism = Adeno-associated virus
SEQUENCE: 17
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPAKKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI SSQSGGSTND NTYFGYSTPW GYFDFNRFHC HFSPRDWQRL  300
INNNWGFRPK KLNFKLFNIQ VKEVTTNDGT TTIANNLTST VQVFTDSEYQ LPYVLGSAHQ  360
GCLPPFPADV FMIPQYGYLT LNNGSQAVGR SSFYCLEYFP SQMLRTGNNF QFSYTFEDVP  420
FHSSYAHSQS LDRLMNPLID QYLYYLSRTQ TTSGTAGNRT LQFSQAGPSS MANQAKNWLP  480
GPCYRQQRVS KTTNQNNNSN FAWTGATKYH LNGRDSLVNP GPAMATHKDD EDKFFPMSGV  540
LIFGKQGAGN SNVDLDNVMI TNEEEIKTTN PVATEEYGTV ATNLQSANTA PATGTVNSQG  600
ALPGMVWQDR DVYLQGPIWA KIPHTDGHFH PSPLMGGFGL KHPPPQILIK NTPVPANPPT  660
TFSPAKFASF ITQYSTGQVS VEIEWELQKE NSKRWNPEIQ YTSNYNKSTN VDFAVDTNGV  720
YSEPRPIGTR YLTRNL                                                  736
```

```
SEQ ID NO: 18          moltype = AA  length = 23
FEATURE                Location/Qualifiers
source                 1..23
                       mol_type = protein
                       organism = Adeno-associated virus
SEQUENCE: 18
HLYKQISSQS GASNDNHYFG YST                                          23

SEQ ID NO: 19          moltype = AA  length = 23
FEATURE                Location/Qualifiers
source                 1..23
                       mol_type = protein
                       organism = Adeno-associated virus
SEQUENCE: 19
HLYKQISSQS GASNDNHYFG YST                                          23

SEQ ID NO: 20          moltype = AA  length = 23
FEATURE                Location/Qualifiers
source                 1..23
                       mol_type = protein
                       organism = Adeno-associated virus
SEQUENCE: 20
HLYKQISSQS GASNDNHYFG YST                                          23

SEQ ID NO: 21          moltype = AA  length = 23
FEATURE                Location/Qualifiers
source                 1..23
                       mol_type = protein
                       organism = Adeno-associated virus
SEQUENCE: 21
HLYKQISSQS GASNDNHYFG YST                                          23

SEQ ID NO: 22          moltype = AA  length = 20
FEATURE                Location/Qualifiers
source                 1..20
                       mol_type = protein
                       organism = Adeno-associated virus
SEQUENCE: 22
HLYKRLGESL QSNTYNGFST                                              20

SEQ ID NO: 23          moltype = AA  length = 20
FEATURE                Location/Qualifiers
source                 1..20
                       mol_type = protein
                       organism = Adeno-associated virus
SEQUENCE: 23
HLYLRLGTTS NSNTYNGFST                                              20

SEQ ID NO: 24          moltype = AA  length = 24
FEATURE                Location/Qualifiers
source                 1..24
                       mol_type = protein
                       organism = Adeno-associated virus
SEQUENCE: 24
HQYREIKSGS VDGSNANAYF GYST                                         24

SEQ ID NO: 25          moltype = AA  length = 24
FEATURE                Location/Qualifiers
source                 1..24
                       mol_type = protein
                       organism = Adeno-associated virus
SEQUENCE: 25
HLYKQISSAS TGASNDNHYF GYST                                         24

SEQ ID NO: 26          moltype = AA  length = 24
FEATURE                Location/Qualifiers
source                 1..24
                       mol_type = protein
                       organism = Adeno-associated virus
SEQUENCE: 26
HLYKQISSET AGSTNDNTYF GYST                                         24

SEQ ID NO: 27          moltype = AA  length = 25
FEATURE                Location/Qualifiers
source                 1..25
                       mol_type = protein
                       organism = Adeno-associated virus
SEQUENCE: 27
```

-continued

```
HLYKQISNGT SGGATNDNTY FGYST                                            25

SEQ ID NO: 28          moltype = AA  length = 25
FEATURE                Location/Qualifiers
source                 1..25
                       mol_type = protein
                       organism = Adeno-associated virus
SEQUENCE: 28
HLYKQISNGT SGGSTNDNTY FGYST                                            25

SEQ ID NO: 29          moltype = AA  length = 25
FEATURE                Location/Qualifiers
source                 1..25
                       mol_type = protein
                       organism = Adeno-associated virus
SEQUENCE: 29
HLYKQISNGT SGGSTNDNTY FGYST                                            25

SEQ ID NO: 30          moltype = AA  length = 25
FEATURE                Location/Qualifiers
source                 1..25
                       mol_type = protein
                       organism = Adeno-associated virus
SEQUENCE: 30
HLYKQISNST SGGSSNDNAY FGYST                                            25

SEQ ID NO: 31          moltype = AA  length = 24
FEATURE                Location/Qualifiers
source                 1..24
                       mol_type = protein
                       organism = Adeno-associated virus
SEQUENCE: 31
HLYKQISSQS GGSTNDNTYF GYST                                             24

SEQ ID NO: 32          moltype = AA  length = 25
FEATURE                Location/Qualifiers
source                 1..25
                       mol_type = protein
                       organism = Adeno-associated virus
SEQUENCE: 32
HLYKQISNSQ SGGSTNDNTY FGYST                                            25

SEQ ID NO: 33          moltype = AA  length = 25
FEATURE                Location/Qualifiers
source                 1..25
                       mol_type = protein
                       organism = Adeno-associated virus
SEQUENCE: 33
HLYKQISNGT SGGSTNDNTY FGYST                                            25

SEQ ID NO: 34          moltype = AA  length = 25
FEATURE                Location/Qualifiers
source                 1..25
                       mol_type = protein
                       organism = Adeno-associated virus
SEQUENCE: 34
HLYKQISNGT SGGSTNDNTY FGYST                                            25

SEQ ID NO: 35          moltype = AA  length = 25
FEATURE                Location/Qualifiers
source                 1..25
                       mol_type = protein
                       organism = Adeno-associated virus
SEQUENCE: 35
HLYKQISNGT SGGSTNDNTY FGYST                                            25

SEQ ID NO: 36          moltype = AA  length = 25
FEATURE                Location/Qualifiers
source                 1..25
                       mol_type = protein
                       organism = Adeno-associated virus
SEQUENCE: 36
HLYKQISNGT SGGSTNDNTY FGYST                                            25

SEQ ID NO: 37          moltype = AA  length = 24
FEATURE                Location/Qualifiers
source                 1..24
                       mol_type = protein
                       organism = Adeno-associated virus
```

-continued

```
SEQUENCE: 37
HLYKQISSQS AGSTNDNTYF GYST                                    24

SEQ ID NO: 38           moltype = AA  length = 23
FEATURE                 Location/Qualifiers
source                  1..23
                        mol_type = protein
                        organism = Adeno-associated virus
SEQUENCE: 38
HLYKQISSQS GASNDNHYFG YST                                     23

SEQ ID NO: 39           moltype = AA  length = 23
FEATURE                 Location/Qualifiers
source                  1..23
                        mol_type = protein
                        organism = Adeno-associated virus
SEQUENCE: 39
HLYKQISSQS GASNDNHYFG YST                                     23

SEQ ID NO: 40           moltype = AA  length = 10
FEATURE                 Location/Qualifiers
source                  1..10
                        mol_type = protein
                        organism = Adeno-associated virus
SEQUENCE: 40
SQSGGSTNDN                                                    10

SEQ ID NO: 41           moltype = AA  length = 10
FEATURE                 Location/Qualifiers
source                  1..10
                        mol_type = protein
                        organism = Adeno-associated virus
SEQUENCE: 41
SQSGASTNDN                                                    10

SEQ ID NO: 42           moltype = AA  length = 9
FEATURE                 Location/Qualifiers
source                  1..9
                        mol_type = protein
                        organism = Adeno-associated virus
SEQUENCE: 42
SQSGASNDN                                                     9

SEQ ID NO: 43           moltype = AA  length = 9
FEATURE                 Location/Qualifiers
source                  1..9
                        mol_type = protein
                        organism = Adeno-associated virus
SEQUENCE: 43
SQSGASNDN                                                     9

SEQ ID NO: 44           moltype = AA  length = 9
FEATURE                 Location/Qualifiers
source                  1..9
                        mol_type = protein
                        organism = Adeno-associated virus
SEQUENCE: 44
SQSGGSNDN                                                     9

SEQ ID NO: 45           moltype = AA  length = 10
FEATURE                 Location/Qualifiers
source                  1..10
                        mol_type = protein
                        organism = Adeno-associated virus
SEQUENCE: 45
SQSGASTNDN                                                    10

SEQ ID NO: 46           moltype = AA  length = 10
FEATURE                 Location/Qualifiers
source                  1..10
                        mol_type = protein
                        organism = Adeno-associated virus
SEQUENCE: 46
SQSGGSTNDN                                                    10

SEQ ID NO: 47           moltype = AA  length = 9
FEATURE                 Location/Qualifiers
source                  1..9
                        mol_type = protein
```

-continued

```
                        organism = Adeno-associated virus
SEQUENCE: 47
SQSGATNDN                                                   9

SEQ ID NO: 48           moltype = AA  length = 10
FEATURE                 Location/Qualifiers
source                  1..10
                        mol_type = protein
                        organism = Adeno-associated virus
SEQUENCE: 48
SQSGAASNDN                                                  10

SEQ ID NO: 49           moltype = AA  length = 10
FEATURE                 Location/Qualifiers
source                  1..10
                        mol_type = protein
                        organism = Adeno-associated virus
SEQUENCE: 49
SQSGGASNDN                                                  10

SEQ ID NO: 50           moltype = AA  length = 10
FEATURE                 Location/Qualifiers
source                  1..10
                        mol_type = protein
                        organism = Adeno-associated virus
SEQUENCE: 50
SQSGAATNDN                                                  10

SEQ ID NO: 51           moltype = AA  length = 10
FEATURE                 Location/Qualifiers
source                  1..10
                        mol_type = protein
                        organism = Adeno-associated virus
SEQUENCE: 51
SQSGGATNDN                                                  10

SEQ ID NO: 52           moltype = AA  length = 11
FEATURE                 Location/Qualifiers
source                  1..11
                        mol_type = protein
                        organism = Adeno-associated virus
SEQUENCE: 52
NSTSGGSSND N                                                11

SEQ ID NO: 53           moltype = AA  length = 11
FEATURE                 Location/Qualifiers
source                  1..11
                        mol_type = protein
                        organism = Adeno-associated virus
SEQUENCE: 53
NSTSGASSND N                                                11

SEQ ID NO: 54           moltype = AA  length = 11
FEATURE                 Location/Qualifiers
source                  1..11
                        mol_type = protein
                        organism = Adeno-associated virus
SEQUENCE: 54
NSTSGGSTND N                                                11

SEQ ID NO: 55           moltype = AA  length = 11
FEATURE                 Location/Qualifiers
source                  1..11
                        mol_type = protein
                        organism = Adeno-associated virus
SEQUENCE: 55
NSTSGASTND N                                                11

SEQ ID NO: 56           moltype = AA  length = 10
FEATURE                 Location/Qualifiers
source                  1..10
                        mol_type = protein
                        organism = Adeno-associated virus
SEQUENCE: 56
SQSGGSTNDN                                                  10

SEQ ID NO: 57           moltype = AA  length = 10
FEATURE                 Location/Qualifiers
source                  1..10
```

-continued

```
                        mol_type = protein
                        organism = Adeno-associated virus
SEQUENCE: 57
SQSGASTNDN                                                                  10

SEQ ID NO: 58           moltype = AA  length = 9
FEATURE                 Location/Qualifiers
source                  1..9
                        mol_type = protein
                        organism = Adeno-associated virus
SEQUENCE: 58
SQSGASNDN                                                                   9

SEQ ID NO: 59           moltype = AA  length = 10
FEATURE                 Location/Qualifiers
source                  1..10
                        mol_type = protein
                        organism = Adeno-associated virus
SEQUENCE: 59
SQSGGSTNDN                                                                  10

SEQ ID NO: 60           moltype = AA  length = 10
FEATURE                 Location/Qualifiers
source                  1..10
                        mol_type = protein
                        organism = Adeno-associated virus
SEQUENCE: 60
SQSGASTNDN                                                                  10

SEQ ID NO: 61           moltype = AA  length = 11
FEATURE                 Location/Qualifiers
source                  1..11
                        mol_type = protein
                        organism = Adeno-associated virus
SEQUENCE: 61
NSTSGGSSND N                                                                11

SEQ ID NO: 62           moltype = AA  length = 11
FEATURE                 Location/Qualifiers
source                  1..11
                        mol_type = protein
                        organism = Adeno-associated virus
SEQUENCE: 62
NSTSGGSSND N                                                                11

SEQ ID NO: 63           moltype = AA  length = 9
FEATURE                 Location/Qualifiers
source                  1..9
                        mol_type = protein
                        organism = Adeno-associated virus
SEQUENCE: 63
SQSGASNDN                                                                   9

SEQ ID NO: 64           moltype = AA  length = 41
FEATURE                 Location/Qualifiers
source                  1..41
                        mol_type = protein
                        organism = Adeno-associated virus
SEQUENCE: 64
TAPGKKRPVE HSPVEPDSSS GTGKAGQQPA RKRLNFGQTG D                               41

SEQ ID NO: 65           moltype = AA  length = 41
FEATURE                 Location/Qualifiers
source                  1..41
                        mol_type = protein
                        organism = Adeno-associated virus
SEQUENCE: 65
TAPGKKRPVD QSPQEPDSSS GVGKSGKQPA RKRLNFGQTG D                               41

SEQ ID NO: 66           moltype = AA  length = 41
FEATURE                 Location/Qualifiers
source                  1..41
                        mol_type = protein
                        organism = Adeno-associated virus
SEQUENCE: 66
TAPGKKRPVD QSPQEPDSSS GVGKSGKQPA RKRLNFGQTG D                               41

SEQ ID NO: 67           moltype = AA  length = 41
FEATURE                 Location/Qualifiers
```

-continued

```
source                  1..41
                        mol_type = protein
                        organism = Adeno-associated virus
SEQUENCE: 67
TAPGKKRPVE HSPVEPDSSS GTGKAGQRPA RKRLNFGQTG D                    41

SEQ ID NO: 68           moltype = AA  length = 37
FEATURE                 Location/Qualifiers
source                  1..37
                        mol_type = protein
                        organism = Adeno-associated virus
SEQUENCE: 68
TAPGKKRPLI ESPQQPDSST GIGKKGKQPA KKKLVFE                         37

SEQ ID NO: 69           moltype = AA  length = 36
FEATURE                 Location/Qualifiers
source                  1..36
                        mol_type = protein
                        organism = Adeno-associated virus
SEQUENCE: 69
TAPGKKRPLE SPQEPDSSSG IGKKGKQPAK KRLNFE                          36

SEQ ID NO: 70           moltype = AA  length = 21
FEATURE                 Location/Qualifiers
source                  1..21
                        mol_type = protein
                        organism = Adeno-associated virus
SEQUENCE: 70
TAPTGKRIDD HFPKRKKART E                                          21

SEQ ID NO: 71           moltype = AA  length = 41
FEATURE                 Location/Qualifiers
source                  1..41
                        mol_type = protein
                        organism = Adeno-associated virus
SEQUENCE: 71
TAPGKKRPVE QSPQEPDSSS GIGKTGQQPA KKRLNFGQTG D                    41

SEQ ID NO: 72           moltype = AA  length = 42
FEATURE                 Location/Qualifiers
source                  1..42
                        mol_type = protein
                        organism = Adeno-associated virus
SEQUENCE: 72
TAPAKKRPVE PSPQRSPDSS TGIGKKGQQP ARKRLNFGQT GD                   42

SEQ ID NO: 73           moltype = AA  length = 42
FEATURE                 Location/Qualifiers
source                  1..42
                        mol_type = protein
                        organism = Adeno-associated virus
SEQUENCE: 73
TAPGKKRPVE PSPQRSPDSS TGIGKKGQQP ARKRLNFGQT GD                   42

SEQ ID NO: 74           moltype = AA  length = 42
FEATURE                 Location/Qualifiers
source                  1..42
                        mol_type = protein
                        organism = Adeno-associated virus
SEQUENCE: 74
TAPGKKRPVE PSPQRSPDSS TGIGKKGQQP AKKRLNFGQT GD                   42

SEQ ID NO: 75           moltype = AA  length = 42
FEATURE                 Location/Qualifiers
source                  1..42
                        mol_type = protein
                        organism = Adeno-associated virus
SEQUENCE: 75
TAPGKKRPVE PSPQRSPDSS TGIGKKGQQP AKKRLNFGQT GD                   42

SEQ ID NO: 76           moltype = AA  length = 41
FEATURE                 Location/Qualifiers
source                  1..41
                        mol_type = protein
                        organism = Adeno-associated virus
SEQUENCE: 76
TAPGKKRPVE QSPQEPDSSA GIGKSGAQPA KKRLNFGQTG D                    41

SEQ ID NO: 77           moltype = AA  length = 41
```

-continued

```
FEATURE                Location/Qualifiers
source                 1..41
                       mol_type = protein
                       organism = Adeno-associated virus
SEQUENCE: 77
TAPGKKRPVE QSPQEPDSSS GIGKKGQQPA RKRLNFGQTG D                      41

SEQ ID NO: 78          moltype = AA  length = 41
FEATURE                Location/Qualifiers
source                 1..41
                       mol_type = protein
                       organism = Adeno-associated virus
SEQUENCE: 78
TAPGKKRPVE QSPQEPDSST GIGKKGQQPA KKRLNFGQTG D                      41

SEQ ID NO: 79          moltype = AA  length = 42
FEATURE                Location/Qualifiers
source                 1..42
                       mol_type = protein
                       organism = Adeno-associated virus
SEQUENCE: 79
TAPGKKRPVE QSPQREPDSS TGIGKKGQQP AKKRLNFGQT GD                     42

SEQ ID NO: 80          moltype = AA  length = 42
FEATURE                Location/Qualifiers
source                 1..42
                       mol_type = protein
                       organism = Adeno-associated virus
SEQUENCE: 80
TAPGKKRPVE QSPQREPDSS TGIGKKGQQP ARKRLNFGQT GD                     42

SEQ ID NO: 81          moltype = AA  length = 42
FEATURE                Location/Qualifiers
source                 1..42
                       mol_type = protein
                       organism = Adeno-associated virus
SEQUENCE: 81
TAPGKKRPVE PSPQRSPDSS TGIGKKGQQP ARKRLNFGQT GD                     42

SEQ ID NO: 82          moltype = AA  length = 41
FEATURE                Location/Qualifiers
source                 1..41
                       mol_type = protein
                       organism = Adeno-associated virus
SEQUENCE: 82
TAPGKKRPVE QSPQEPDSSS GIGKTGQQPA KKRLNFGQTG D                      41

SEQ ID NO: 83          moltype = AA  length = 42
FEATURE                Location/Qualifiers
source                 1..42
                       mol_type = protein
                       organism = Adeno-associated virus
SEQUENCE: 83
TAPGKKRPVE PSPQRSPDSS TGIGKKGQQP AKKRLNFGQT GD                     42

SEQ ID NO: 84          moltype = AA  length = 41
FEATURE                Location/Qualifiers
source                 1..41
                       mol_type = protein
                       organism = Adeno-associated virus
SEQUENCE: 84
TAPGKKRPVE QSPQEPDSSS GIGKSGQQPA KKRLNFGQTG D                      41

SEQ ID NO: 85          moltype = AA  length = 41
FEATURE                Location/Qualifiers
source                 1..41
                       mol_type = protein
                       organism = Adeno-associated virus
SEQUENCE: 85
TAPGKKRPVE QSPQEPDSSS GIGKSGQQPA RKRLNFGQTG D                      41

SEQ ID NO: 86          moltype = DNA  length = 110
FEATURE                Location/Qualifiers
source                 1..110
                       mol_type = genomic DNA
                       organism = Adeno-associated virus
SEQUENCE: 86
tgcccactta caacaaccat ctctacaagc aaatctccag ccaatcagga gcttcaaacg  60
acaaccacta ctttggctac agcacccctt gggggtattt tgactttaac             110
```

```
SEQ ID NO: 87          moltype = AA  length = 734
FEATURE                Location/Qualifiers
source                 1..734
                       mol_type = protein
                       organism = synthetic construct
SEQUENCE: 87
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SSQSGASNDN AYFGYSTPWG YFDFNRFHCH FSPRDWQRLI  300
NNNWGFRPKR LNFKLFNIQV KEVTDNNGVK TIANNLTSTV QVFTDSDYQL PYVLGSAHEG  360
CLPPFPADVF MIPQYGYLTL NDGSQAVGRS SFYCLEYFPS QMLRTGNNFQ FSYEFENVPF  420
HSSYAHSQSL DRLMNPLIDQ YLYYLSKTIN GSGQNQQTLK FSVAGPSNMA VQGRNYIPGP  480
SYRQQRVSTT VTQNNNSEFA WPGASSWALN GRNSLMNPGP AMASHKEGED RFFPLSGSLI  540
FGKQGTGRDN VDADKVMITN EEEIKTTNPV ATESYGQVAT NHQSAQAQAQ TGWVQNQGIL  600
PGMVWQDRDV YLQGPIWAKI PHTDGNFHPS PLMGGFGMKH PPPQILIKNT PVPADPPTAF  660
NKDKLNSFIT QYSTGQVSVE IEWELQKENS KRWNPEIQYT SNYYKSNNVE FAVNTEGVYS  720
EPRPIGTRYL TRNL                                                    734

SEQ ID NO: 88          moltype = AA  length = 735
FEATURE                Location/Qualifiers
source                 1..735
                       mol_type = protein
                       organism = synthetic construct
SEQUENCE: 88
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPARKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI SSQSGASNDN TYFGYSTPWG YFDFNRFHCH FSPRDWQRLI  300
NNNWGFRPKK LNFKLFNIQV KEVTTNDGTT TIANNLTSTV QVFTDSEYQL PYVLGSAHQG  360
CLPPFPADVF MIPQYGYLTL NNGSQAVGRS SFYCLEYFPS QMLRTGNNFQ FSYTFEDVPF  420
HSSYAHSQSL DRLMNPLIDQ YLYYLSRTQT TSGTAGNRTL QFSQAGPSSM ANQAKNWLPG  480
PCYRQQRVSK TTNQNNNSNF AWTGATKYHL NGRDSLVNPG PAMATHKDDE DKFFPMSGVL  540
IFGKQGAGNS NVDLDNVMIT NEEEIKTTNP VATEEYGTVA TNLQSANTAP ATGTVNSQGA  600
LPGMVWQDRD VYLQGPIWAK IPHTDGHFHP SPLMGGFGLK HPPPQILIKN TPVPANPPTT  660
FSPAKFASFI TQYSTGQVSV EIEWELQKEN SKRWNPEIQY TSNYNKSTNV DFAVDTNGVY  720
SEPRPIGTRY LTRNL                                                   735

SEQ ID NO: 89          moltype = AA  length = 736
FEATURE                Location/Qualifiers
source                 1..736
                       mol_type = protein
                       organism = synthetic construct
SEQUENCE: 89
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPARKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI NSTSGGSSND NTYFGYSTPW GYFDFNRFHC HFSPRDWQRL  300
INNNWGFRPK KLNFKLFNIQ VKEVTTNDGT TTIANNLTST VQVFTDSEYQ LPYVLGSAHQ  360
GCLPPFPADV FMIPQYGYLT LNNGSQAVGR SSFYCLEYFP SQMLRTGNNF QFSYTFEDVP  420
FHSSYAHSQS LDRLMNPLID QYLYYLSRTQ TTSGTAGNRT LQFSQAGPSS MANQAKNWLP  480
GPCYRQQRVS KTTNQNNNSN FAWTGATKYH LNGRDSLVNP GPAMATHKDD EDKFFPMSGV  540
LIFGKQGAGN SNVDLDNVMI TNEEEIKTTN PVATEEYGTV ATNLQSANTA PATGTVNSQG  600
ALPGMVWQDR DVYLQGPIWA KIPHTDGHFH PSPLMGGFGL KHPPPQILIK NTPVPANPPT  660
TFSPAKFASF ITQYSTGQVS VEIEWELQKE NSKRWNPEIQ YTSNYNKSTN VDFAVDTNGV  720
YSEPRPIGTR YLTRNL                                                  736

SEQ ID NO: 90          moltype = AA  length = 736
FEATURE                Location/Qualifiers
source                 1..736
                       mol_type = protein
                       organism = synthetic construct
SEQUENCE: 90
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKRPVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGATNDN HYFGYSTPWG YFDFNRFHCH FSPRDWQRLI  300
NNNWGFRPKK LSFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
```

-continued

| | | | | | |
|---|---|---|---|---|---|
| HSSYAHSQSL | DRLMNPLIDQ | YLYYLNRTQG | TTSGTTNQSR | LLFSQAGPQS | MSLQARNWLP 480 |
| GPCYRQQRLS | KTANDNNNSN | FPWTAASKYH | LNGRDSLVNP | GPAMASHKDD | EEKFFPMHGN 540 |
| LIFGKEGTTA | SNAELDNVMI | TDEEEIRTTN | PVATEQYGTV | ANNLQSSNTA | PTTRTVNDQG 600 |
| ALPGMVWQDR | DVYLQGPIWA | KIPHTDGHFH | PSPLMGGFGL | KHPPPQIMIK | NTPVPANPPT 660 |
| TFSPAKFASF | ITQYSTGQVS | VEIEWELQKE | NSKRWNPEIQ | YTSNYNKSVN | VDFTVDTNGV 720 |
| YSEPRPIGTR | YLTRNL | | | | 736 |